US008101371B2

(12) United States Patent
Moussa et al.

(10) Patent No.: US 8,101,371 B2
(45) Date of Patent: Jan. 24, 2012

(54) METHODS FOR THE DIAGNOSIS OF GENITOURINARY CANCER

(75) Inventors: Omar Moussa, Mount Pleasant, SC (US); Dennis K. Watson, Mount Pleasant, SC (US); Perry V. Halushka, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 12/253,592

(22) Filed: Oct. 17, 2008

(65) Prior Publication Data

US 2009/0136972 A1 May 28, 2009

Related U.S. Application Data

(60) Provisional application No. 60/980,917, filed on Oct. 18, 2007.

(51) Int. Cl.
*G01N 33/53* (2006.01)
*G01N 33/574* (2006.01)

(52) U.S. Cl. ...................... 435/7.23; 435/7.1

(58) Field of Classification Search .................. None
See application file for complete search history.

(56) References Cited

U.S. PATENT DOCUMENTS

| 7,459,531 | B2 | 12/2008 | Moore et al. ............. 530/350 |
| 2001/0006633 | A1 | 7/2001 | Kirn .......................... 424/93.6 |
| 2002/0028799 | A1 | 3/2002 | Naylor et al. ............ 514/210.21 |
| 2003/0119714 | A1 | 6/2003 | Naylor et al. .................. 514/410 |
| 2003/0124132 | A1 | 7/2003 | Thorpe et al. ............. 424/178.1 |
| 2003/0129193 | A1 | 7/2003 | Thorpe et al. ............. 424/155.1 |
| 2004/0053880 | A1 | 3/2004 | Krieg ........................ 536/23.72 |
| 2004/0067905 | A1 | 4/2004 | Krieg .......................... 536/23.1 |
| 2004/0092472 | A1 | 5/2004 | Krieg .......................... 424/85.1 |
| 2004/0225077 | A1 | 11/2004 | Gravett et al. .................. 424/486 |
| 2005/0089894 | A1 | 4/2005 | Ginns et al. ..................... 702/20 |
| 2005/0281883 | A1 | 12/2005 | Daniloff et al. ................ 424/423 |
| 2006/0018917 | A1 | 1/2006 | Faris et al. .................. 424/185.1 |
| 2006/0041014 | A1 | 2/2006 | Naylor et al. .................. 514/516 |
| 2006/0069161 | A1 | 3/2006 | Lee et al. ...................... 514/571 |
| 2006/0088539 | A1 | 4/2006 | Bander ...................... 424/155.1 |

FOREIGN PATENT DOCUMENTS

| EP | 0234729 A2 | 9/1987 |
| WO | WO 97/18805 | 5/1997 |
| WO | WO 97/32585 | 9/1997 |
| WO | WO 99/50454 | 10/1999 |
| WO | WO 01/21009 | 3/2001 |
| WO | WO 01/39777 | 6/2001 |
| WO | WO 02/03995 | 1/2002 |
| WO | WO 02/47670 | 6/2002 |
| WO | WO 03/028840 | 4/2003 |
| WO | WO 03/042403 | 5/2003 |
| WO | WO 03/061596 | 7/2003 |
| WO | WO 2004/005476 | 1/2004 |
| WO | WO 2004/060346 | 7/2004 |
| WO | WO 2004/060405 | 7/2004 |
| WO | WO 2005/014850 | 2/2005 |
| WO | WO 2005/051871 | 6/2005 |
| WO | WO 2006/004803 | 1/2006 |
| WO | WO 2006/034128 | 3/2006 |
| WO | WO 2006/083260 | 8/2006 |
| WO | WO 2006/121522 | 11/2006 |

OTHER PUBLICATIONS

Nie et al, Cancer Res., 68:115-121, 2008.*
Moussa et al, Cancer Res. 65:11581-11587, 2005.*
Dassesse et al, European Urology 50:1021-31, 2006.*
Mesh word search result, 2010.*
Google search result, 2010.*
Ali-Eldein et al., "Comparison of urinary cytology, telomerase NMP22 and DNA flow cytometry in the detection and surveillance of bladder cancer," 167 (4): 645, 2002.
Ashton and Ware, "Thromboxane A2 receptor signaling inhibits vascular endothelial growth factor-induced endothelial cell differentiation and migration" *Circ. Res.*, 95 (4): 372-379, 2004.
Brightling et al., "Isoprenaline inhibits thromboxane B2 release from U937 cells," *J. Leukoc. Biol.*, 53 (5): 559-562, 1993.
Coyle and Kinsella, "Synthetic peroxisome proliferator-activated receptor gamma agonists rosiglitazone and troglitazone suppress transcription by promoter 3 of the human thromboxane A2 receptor gene in human erythroleukemia cells." *Biochem. Pharmacol.*, 71 (9): 1308-1323, 2006.
Coyle et al., "15-deoxy Delta12,14-prostaglandin J2 suppresses transcription by promoter 3 of the human thromboxane A2 receptor gene through peroxisome proliferator-activated receptor gamma in human erythroleukemia cellsm," *FEBS J.*, 272 (18): 4754-4773, 2005.
Dannon et al., "Eicosanoid synthesis by cultured human urothelial cells: potential role in bladder cancer," *Cancer Res.*, 46 (11): 5676-5681, 1986.
Fels et al., "Early urinary markers of target nephron segments as studied in cadmium toxcity," *Kidney Int. Supp.*, 47: S81-88, 1994.
Klahr, "Mechanisms of progression of chronic renal damage," *J. Nephrol.*, 12 Suppl. 2: S53-62, 1999.
Morrow et al., "Increased formation of thromboxane in vivo in humans with mastocytosis," *J. Invest. Dermatol.*, 113 (1): 93-97, 1999.
Moussa et al., "Increased expression of thromboxane A2 signaling pathway components in bladder cancer: Association with pathogenesis and poor prognosis," *Prostaglandins and Other Lipid Mediators*, 79 (1-2): 147-148, 2006.
Moussa et al., "Inhibition of thromboxane synthase activity modulates bladder cancer cell responses to chemotherapeutic agents," *Oncogene*, 2007.
Moussa et al., "Prognostic and functional significance of thromboxane synthase gene overexpression in invasive bladder cancer," *Cancer Res.*, 65 (24): 11581-11587, 2004.

(Continued)

Primary Examiner — Misook Yu
Assistant Examiner — Lei Yao
(74) *Attorney, Agent, or Firm* — Fulbright & Jaworski

(57) ABSTRACT

Methods for the diagnosis of genitourinary (GU) cancer are provided. In particular, urine has been found to contain significant levels of thromboxane receptor β (TPβ) methods for diagnosing GU cancer. Methods for assessing treatment, prognosing and staging GU cancers, as well as kits therefor, also are provided.

10 Claims, 2 Drawing Sheets

OTHER PUBLICATIONS

Moussa et al., "Thromboxane (TP) beta receptor in human bladder cancer: role in pathogensis and prognosis," *Proceedings of the American Association for Cancer Research Annual Meeting*, 48: 643, 2007.

Penning et al., "Ca (2+)-mediated prostaglandin E2 induction reduces haematoporphyric-derivative-induced cytotoxicity of T24 human bladdar transitional carcinoma cells in vitro," *Biochem. J.*, 292 (pt. 1): 237-240, 1993.

Suzuki et al., "Human bronchial smooth muscle cell proliferation via thromboxane A2 receptor," *Prostaglandins Leukot. Essent. Fatty Acids*, 71 (6): 375-382, 2004.

International Search Report and Written Opinion, issued in Application No. PCT/US 08/80306, dated Jan. 22, 2009.

Moussa et al., "Prognostic and functional significance of thromboxane synthase gene overexpression in invasive bladder cancer," *Cancer Res.*, 65:11581-11587, 2005.

* cited by examiner

SEQUENCE LISTING

<160> NUMBER OF SEQ ID NOS: 9

<210> SEQ ID NO 1
<211> LENGTH: 2446

```
<212> TYPE: DNA
<213> ORGANISM: Homo sapiens
<220> FEATURE:
<221> NAME/KEY: CDS
<222> LOCATION: (215)..(1246)

<400> SEQUENCE: 1
ccctctgccc gccccagcc ctcgccccac cctcggcgcc cgcacatctg cctgctcagc      60
tccagacggc gccggaccc ccgggcgcgg gatccagcca ggtgggagcc ccgcagatga     120
ggtctctgaa ggtgtgcctg aaccagtgcc agcctgccct gtctgcagca tcggcctgat    180
ggggtggtga ctgatccctc agggctccgg agcc atg tgg ccc aac ggc agt tcc   235
                                    Met Trp Pro Asn Gly Ser Ser
                                     1               5 ctg ggg ccc tgt ttc cgg ccc aca aac att acc ctg gag gag aga cgg     283
Leu Gly Pro Cys Phe Arg Pro Thr Asn Ile Thr Leu Glu Glu Arg Arg
        10                  15                  20 ctg atc gcc tcg ccc tgg ttc gcc gcc tcc ttc tgc gtg gtg ggc ctg     331
Leu Ile Ala Ser Pro Trp Phe Ala Ala Ser Phe Cys Val Val Gly Leu
25                  30                  35 gcc tcc aac ctg ctg gcc ctg agc gtg ctg gcg ggc gcg cgg cag ggg     379
Ala Ser Asn Leu Leu Ala Leu Ser Val Leu Ala Gly Ala Arg Gln Gly
40                  45                  50                  55 ggt tcg cac acg cgc tcc tcc ttc ctc acc ttc ctc tgc ggc ctc gtc     427
Gly Ser His Thr Arg Ser Ser Phe Leu Thr Phe Leu Cys Gly Leu Val
            60                  65                  70 ctc acc gac ttc ctg ggg ctg ctg gtg acc ggt acc atc gtg gtg tcc     475
Leu Thr Asp Phe Leu Gly Leu Leu Val Thr Gly Thr Ile Val Val Ser
            75                  80                  85 cag cac gcc gcg ctc ttc gag tgg cac gcc gtg gac cct ggc tgc cgt     523
Gln His Ala Ala Leu Phe Glu Trp His Ala Val Asp Pro Gly Cys Arg
            90                  95                 100 ctc tgt cgc ttc atg ggc gtc gtc atg atc ttc ttc ggc ctg tcc ccg     571
Leu Cys Arg Phe Met Gly Val Val Met Ile Phe Phe Gly Leu Ser Pro
        105                 110                 115 ctg ctg ctg ggg gcc gcc atg gcc tca gag cgc tac ctg ggt atc acc     619
Leu Leu Leu Gly Ala Ala Met Ala Ser Glu Arg Tyr Leu Gly Ile Thr
120                 125                 130                 135 cgg ccc ttc tcg cgc ccg gcg gtc gcc tcg cag cgc gcc tgg gcc         667
Arg Pro Phe Ser Arg Pro Ala Val Ala Ser Gln Arg Arg Ala Trp Ala
                140                 145                 150 acc gtg ggg ctg gtg tgg gcg gcc gcg ctg gcg ctg ggc ctg ctg ccc     715
Thr Val Gly Leu Val Trp Ala Ala Ala Leu Ala Leu Gly Leu Leu Pro
                155                 160                 165 ctg ctg ggc gtg ggt cgc tac acc gtg caa tac ccg ggg tcc tgg tgc     763
Leu Leu Gly Val Gly Arg Tyr Thr Val Gln Tyr Pro Gly Ser Trp Cys
            170                 175                 180 ttc ctg acg ctg ggc gcc gag tcc ggg gac gtg gcc ttc ggg ctg ctc     811
Phe Leu Thr Leu Gly Ala Glu Ser Gly Asp Val Ala Phe Gly Leu Leu
        185                 190                 195 ttc tcc atg ctg ggc ggc ctc tcg gtc ggg ctg tcc ttc ctg ctg aac     859
Phe Ser Met Leu Gly Gly Leu Ser Val Gly Leu Ser Phe Leu Leu Asn
200                 205                 210                 215 acg gtc agc gtg gcc acc ctg tgc cac gtc tac cac ggg cag gag gcg     907
Thr Val Ser Val Ala Thr Leu Cys His Val Tyr His Gly Gln Glu Ala
                220                 225                 230 gcc cag cag cgt ccc cgg gac tcc gag gtg gag atg atg gct cag ctc     955
Ala Gln Gln Arg Pro Arg Asp Ser Glu Val Glu Met Met Ala Gln Leu
                235                 240                 245 ctg ggg atc atg gtg gtg gcc agc gtg tgt tgg ctg ccc ctt ctg gtc    1003
Leu Gly Ile Met Val Val Ala Ser Val Cys Trp Leu Pro Leu Leu Val
```

```
ttc atc gcc cag aca gtg ctg cga aac ccg cct gcc atg agc ccc gcc    1051
Phe Ile Ala Gln Thr Val Leu Arg Asn Pro Pro Ala Met Ser Pro Ala
265                 270                 275 ggg cag ctg tcc cgc acc acg gag aag gag ctg ctc atc tac ttg cgc    1099
Gly Gln Leu Ser Arg Thr Thr Glu Lys Glu Leu Leu Ile Tyr Leu Arg
280                 285                 290                 295 gtg gcc acc tgg aac cag atc ctg gac ccc tgg gtg tat atc ctg ttc    1147
Val Ala Thr Trp Asn Gln Ile Leu Asp Pro Trp Val Tyr Ile Leu Phe
                300                 305                 310 cgc cgc gcc gtg ctc cgg cgt ctc cag cct cgc ctc agc acc cgg ccc    1195
Arg Arg Ala Val Leu Arg Arg Leu Gln Pro Arg Leu Ser Thr Arg Pro
                315                 320                 325 agg tcg ctg tcc ctc cag ccc cag ctc acg cag cgc tcc ggg ctg cag    1243
Arg Ser Leu Ser Leu Gln Pro Gln Leu Thr Gln Arg Ser Gly Leu Gln
                330                 335                 340 tag gaagtggaca gagcgcccct cccgcgcctt ccgcggagc ccttggcccc          1296 tcggacagcc catctgcctg ttctgaggat tcaggggctg ggggtgctgg atggacagtg  1356
ggcatcagca gcagggtttt gggttgaccc caatccaacc cggggacccc caactcctcc  1416
ctgatccttt taccaagcac tctcccttcc tcggcccctt tttcccatcc agagctccca  1476 cccttctct gcgtccctcc caaccccagg aagggcatgc agacattgga gagggtctt   1536 gcattgctat ttttttttt agacggagtc ttgctctgtc ccccaggctg gagtgcagtg   1596
gcgcaatctc agctcactgc aacctccacc tccggggttc aagcgattct cctgcctcag  1656
cctcctgagt agctgggact ataggcgcgc gccaccacgc ccggctaatt tttgtatttt  1716
tagtagagac ggggtttcac cgtgttggcc aggctggtct tgaactcctg acctcaggtg  1776
attcaccagc ctcagcctcc caaagtgctg ggatcacagg catgaaccac cacacctggc  1836 cattttttt tttttttta gacggagtct cactctgtgg cccagcctgg agtacagtgg    1896
cacgatctcg gctcactgca acctccgcct cccgggttca agcgattctc gtgcctcagc  1956
ctcccgagca gctgggatta caggcgtaag ccactgcgcc cggccttgca tgctctttga  2016
ccctgaattt gacctacttg ctggggtaca gttgcttcct tttgaacctc aacagggaa   2076 ggctctgtcc agaaaggatt gaatgtgaac ggggcaccc ctttttcttg ccaaaatata   2136
tctctgcctt tggttttatt ttcctttggg tccagaagtt ttcaatctct ggagtttgtg  2196
cattgggcct cacccggagc agacgagggc agggctggga aggatgggga gggacataga  2256
ggattcggtt cctccccac cttgtttctt gagtgtttcc taatcacttg atgggtggta   2316
ccacctagaa ttcttccagc agcctgtaat gggagggcta caggttagcc ctggaacctg  2376
caatcaaacc accttgaat ctgtgtgtca ttaaaagtag atataaatgg gcaaaaaaaa    2436
aaaaaaaaaa                                                          2446

<210> SEQ ID NO 2
<211> LENGTH: 343
<212> TYPE: PRT
<213> ORGANISM: Homo sapiens

<400> SEQUENCE: 2

Met Trp Pro Asn Gly Ser Ser Leu Gly Pro Cys Phe Arg Pro Thr Asn
1               5                   10                  15

Ile Thr Leu Glu Glu Arg Arg Leu Ile Ala Ser Pro Trp Phe Ala Ala
            20                  25                  30

Ser Phe Cys Val Val Gly Leu Ala Ser Asn Leu Leu Ala Leu Ser Val
        35                  40                  45
```

```
Leu Ala Gly Ala Arg Gln Gly Gly Ser His Thr Arg Ser Ser Phe Leu
     50                  55                  60

Thr Phe Leu Cys Gly Leu Val Leu Thr Asp Phe Gly Leu Leu Val
 65              70                  75                  80

Thr Gly Thr Ile Val Val Ser Gln His Ala Ala Leu Phe Glu Trp His
                     85                  90                  95

Ala Val Asp Pro Gly Cys Arg Leu Cys Arg Phe Met Gly Val Val Met
            100                 105                 110

Ile Phe Phe Gly Leu Ser Pro Leu Leu Gly Ala Ala Met Ala Ser
        115                 120                 125

Glu Arg Tyr Leu Gly Ile Thr Arg Pro Phe Ser Arg Pro Ala Val Ala
    130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                165                 170                 175

Gln Tyr Pro Gly Ser Trp Cys Phe Leu Thr Leu Gly Ala Glu Ser Gly
            180                 185                 190

Asp Val Ala Phe Gly Leu Leu Phe Ser Met Leu Gly Gly Leu Ser Val
        195                 200                 205

Gly Leu Ser Phe Leu Leu Asn Thr Val Ser Val Ala Thr Leu Cys His
    210                 215                 220

Val Tyr His Gly Gln Glu Ala Ala Gln Gln Arg Pro Arg Asp Ser Glu
225                 230                 235                 240

Val Glu Met Met Ala Gln Leu Leu Gly Ile Met Val Val Ala Ser Val
                245                 250                 255

Cys Trp Leu Pro Leu Leu Val Phe Ile Ala Gln Thr Val Leu Arg Asn
            260                 265                 270

Pro Pro Ala Met Ser Pro Ala Gly Gln Leu Ser Arg Thr Thr Glu Lys
        275                 280                 285

Glu Leu Leu Ile Tyr Leu Arg Val Ala Thr Trp Asn Gln Ile Leu Asp
    290                 295                 300

Pro Trp Val Tyr Ile Leu Phe Arg Arg Ala Val Leu Arg Arg Leu Gln
305                 310                 315                 320

Pro Arg Leu Ser Thr Arg Pro Arg Ser Leu Ser Leu Gln Pro Gln Leu
                325                 330                 335

Thr Gln Arg Ser Gly Leu Gln
            340

<210> SEQ ID NO 3
<211> LENGTH: 1785
<212> TYPE: DNA
<213> ORGANISM: Homo sapiens
<220> FEATURE:
<221> NAME/KEY: CDS
<222> LOCATION: (215)..(1324)

<400> SEQUENCE: 3
ccctctgccc gccccagcc ctcgccccac cctcggcgcc cgcacatctg cctgctcagc      60
tccagacggc gcccggaccc ccgggcgcgg gatccagcca ggtgggagcc ccgcagatga    120
ggtctctgaa ggtgtgcctg aaccagtgcc agcctgccct gtctgcagca tcggcctgat    180
ggggtggtga ctgatccctc agggctccgg agcc atg tgg ccc aac ggc agt tcc    235
                                      Met Trp Pro Asn Gly Ser Ser
                                        1               5 ctg ggg ccc tgt ttc cgg ccc aca aac att acc ctg gag gag aga cgg    283
```

```
Leu Gly Pro Cys Phe Arg Pro Thr Asn Ile Thr Leu Glu Glu Arg Arg
        10                  15                  20 ctg atc gcc tcg ccc tgg ttc gcc gcc tcc ttc tgc gtg gtg ggc ctg      331
Leu Ile Ala Ser Pro Trp Phe Ala Ala Ser Phe Cys Val Val Gly Leu
    25                  30                  35 gcc tcc aac ctg ctg gcc ctg agc gtg ctg gcg ggc gcg cgg cag ggg      379
Ala Ser Asn Leu Leu Ala Leu Ser Val Leu Ala Gly Ala Arg Gln Gly
40                  45                  50                  55 ggt tcg cac acg cgc tcc tcc ttc ctc acc ttc ctc tgc ggc ctc gtc      427
Gly Ser His Thr Arg Ser Ser Phe Leu Thr Phe Leu Cys Gly Leu Val
                60                  65                  70 ctc acc gac ttc ctg ggg ctg ctg gtg acc ggt acc atc gtg gtg tcc      475
Leu Thr Asp Phe Leu Gly Leu Leu Val Thr Gly Thr Ile Val Val Ser
                75                  80                  85 cag cac gcc gcg ctc ttc gag tgg cac gcc gtg gac cct ggc tgc cgt      523
Gln His Ala Ala Leu Phe Glu Trp His Ala Val Asp Pro Gly Cys Arg
            90                  95                 100 ctc tgt cgc ttc atg ggc gtc gtc atg atc ttc ttc ggc ctg tcc ccg      571
Leu Cys Arg Phe Met Gly Val Val Met Ile Phe Phe Gly Leu Ser Pro
        105                 110                 115 ctg ctg ctg ggg gcc gcc atg gcc tca gag cgc tac ctg ggt atc acc      619
Leu Leu Leu Gly Ala Ala Met Ala Ser Glu Arg Tyr Leu Gly Ile Thr
120                 125                 130                 135 cgg ccc ttc tcg cgc ccg gcg gtc gcc tcg cag cgc cgc gcc tgg gcc      667
Arg Pro Phe Ser Arg Pro Ala Val Ala Ser Gln Arg Arg Ala Trp Ala
                140                 145                 150 acc gtg ggg ctg gtg tgg gcg gcc gcg ctg gcg ctg ggc ctg ctg ccc      715
Thr Val Gly Leu Val Trp Ala Ala Ala Leu Ala Leu Gly Leu Leu Pro
                155                 160                 165 ctg ctg ggc gtg ggt cgc tac acc gtg caa tac ccg ggg tcc tgg tgc      763
Leu Leu Gly Val Gly Arg Tyr Thr Val Gln Tyr Pro Gly Ser Trp Cys
            170                 175                 180 ttc ctg acg ctg ggc gcc gag tcc ggg gac gtg gcc ttc ggg ctg ctc      811
Phe Leu Thr Leu Gly Ala Glu Ser Gly Asp Val Ala Phe Gly Leu Leu
        185                 190                 195 ttc tcc atg ctg ggc ggc ctc tcg gtc ggg ctg tcc ttc ctg ctg aac      859
Phe Ser Met Leu Gly Gly Leu Ser Val Gly Leu Ser Phe Leu Leu Asn
200                 205                 210                 215 acg gtc agc gtg gcc acc ctg tgc cac gtc tac cac ggg cag gag gcg      907
Thr Val Ser Val Ala Thr Leu Cys His Val Tyr His Gly Gln Glu Ala
                220                 225                 230 gcc cag cag cgt ccc cgg gac tcc gag gtg gag atg atg gct cag ctc      955
Ala Gln Gln Arg Pro Arg Asp Ser Glu Val Glu Met Met Ala Gln Leu
                235                 240                 245 ctg ggg atc atg gtg gtg gcc agc gtg tgt tgg ctg ccc ctt ctg gtc     1003
Leu Gly Ile Met Val Val Ala Ser Val Cys Trp Leu Pro Leu Leu Val
            250                 255                 260 ttc atc gcc cag aca gtg ctg cga aac ccg cct gcc atg agc ccc gcc     1051
Phe Ile Ala Gln Thr Val Leu Arg Asn Pro Pro Ala Met Ser Pro Ala
        265                 270                 275 ggg cag ctg tcc cgc acc acg gag aag gag ctg ctc atc tac ttg cgc     1099
Gly Gln Leu Ser Arg Thr Thr Glu Lys Glu Leu Leu Ile Tyr Leu Arg
280                 285                 290                 295 gtg gcc acc tgg aac cag atc ctg gac ccc tgg gtg tat atc ctg ttc     1147
Val Ala Thr Trp Asn Gln Ile Leu Asp Pro Trp Val Tyr Ile Leu Phe
                300                 305                 310 cgc cgc gcc gtg ctc cgg cgt ctc cag cct cgc ctc agc acc cgg ccc     1195
Arg Arg Ala Val Leu Arg Arg Leu Gln Pro Arg Leu Ser Thr Arg Pro
            315                 320                 325 agc gga gtc tca ctc tgt ggc cca gcc tgg agt aca gtg gca cga tct     1243
```

```
Ser Gly Val Ser Leu Cys Gly Pro Ala Trp Ser Thr Val Ala Arg Ser
            330                 335                 340 cgg ctc act gca acc tcc gcc tcc cgg gtt caa gcg att ctc gtg cct      1291
Arg Leu Thr Ala Thr Ser Ala Ser Arg Val Gln Ala Ile Leu Val Pro
            345                 350                 355 cag cct ccc gag cag ctg gga tta cag gcg taa gccactgcgc ccggccttgc    1344
Gln Pro Pro Glu Gln Leu Gly Leu Gln Ala
360                 365 atgctctttg accctgaatt tgacctactt gctggggtac agttgcttcc ttttgaacct    1404
ccaacaggga aggctctgtc cagaaaggat tgaatgtgaa cggggggcacc ccctttttctt  1464 gccaaaatat atctctgcct ttggttttat tttcctttgg gtccagaagt tttcaatctc    1524
tggagtttgt gcattgggcc tcacccggag cagacgaggg cagggctggg aaggatgggg    1584
agggacatag aggattcggt tcctccccca ccttgtttct tgagtgtttc ctaatcactt    1644
gatgggtggt accacctaga attcttccag cagcctgtaa tgggagggct acaggttagc    1704
cctggaacct gcaatcaaac cacctttgaa tctgtgtgtc attaaaagta gatataaatg    1764
ggcaaaaaaa aaaaaaaaaa a                                              1785

<210> SEQ ID NO 4
<211> LENGTH: 369
<212> TYPE: PRT
<213> ORGANISM: Homo sapiens

<400> SEQUENCE: 4

Met Trp Pro Asn Gly Ser Ser Leu Gly Pro Cys Phe Arg Pro Thr Asn
1               5                   10                  15

Ile Thr Leu Glu Glu Arg Arg Leu Ile Ala Ser Pro Trp Phe Ala Ala
            20                  25                  30

Ser Phe Cys Val Val Gly Leu Ala Ser Asn Leu Leu Ala Leu Ser Val
        35                  40                  45

Leu Ala Gly Ala Arg Gln Gly Gly Ser His Thr Arg Ser Ser Phe Leu
    50                  55                  60

Thr Phe Leu Cys Gly Leu Val Leu Thr Asp Phe Leu Gly Leu Leu Val
65                  70                  75                  80

Thr Gly Thr Ile Val Val Ser Gln His Ala Ala Leu Phe Glu Trp His
                85                  90                  95

Ala Val Asp Pro Gly Cys Arg Leu Cys Arg Phe Met Gly Val Val Met
            100                 105                 110

Ile Phe Phe Gly Leu Ser Pro Leu Leu Leu Gly Ala Ala Met Ala Ser
        115                 120                 125

Glu Arg Tyr Leu Gly Ile Thr Arg Pro Phe Ser Arg Pro Ala Val Ala
    130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                165                 170                 175

Gln Tyr Pro Gly Ser Trp Cys Phe Leu Thr Leu Gly Ala Glu Ser Gly
            180                 185                 190

Asp Val Ala Phe Gly Leu Leu Phe Ser Met Leu Gly Gly Leu Ser Val
        195                 200                 205

Gly Leu Ser Phe Leu Leu Asn Thr Val Ser Val Ala Thr Leu Cys His
    210                 215                 220

Val Tyr His Gly Gln Glu Ala Ala Gln Gln Arg Pro Arg Asp Ser Glu
225                 230                 235                 240
```

-continued

```
Val Glu Met Met Ala Gln Leu Leu Gly Ile Met Val Ala Ser Val
            245                 250                 255

Cys Trp Leu Pro Leu Leu Val Phe Ile Ala Gln Thr Val Leu Arg Asn
        260                 265                 270

Pro Pro Ala Met Ser Pro Ala Gly Gln Leu Ser Arg Thr Thr Glu Lys
        275                 280                 285

Glu Leu Leu Ile Tyr Leu Arg Val Ala Thr Trp Asn Gln Ile Leu Asp
        290                 295                 300

Pro Trp Val Tyr Ile Leu Phe Arg Arg Ala Val Leu Arg Arg Leu Gln
305                 310                 315                 320

Pro Arg Leu Ser Thr Arg Pro Ser Gly Val Ser Leu Cys Gly Pro Ala
            325                 330                 335

Trp Ser Thr Val Ala Arg Ser Arg Leu Thr Ala Thr Ser Ala Ser Arg
            340                 345                 350

Val Gln Ala Ile Leu Val Pro Gln Pro Glu Gln Leu Gly Leu Gln
            355                 360                 365

Ala

<210> SEQ ID NO 5
<211> LENGTH: 22
<212> TYPE: DNA
<213> ORGANISM: Artificial
<220> FEATURE:
<223> OTHER INFORMATION: Synthetic primer

<400> SEQUENCE: 5
acggagaagg agctgctcat ct                                            22

<210> SEQ ID NO 6
<211> LENGTH: 19
<212> TYPE: DNA
<213> ORGANISM: Artificial
<220> FEATURE:
<223> OTHER INFORMATION: Synthetic primer

<400> SEQUENCE: 6
cactgtccat ccagcaccc                                                19

<210> SEQ ID NO 7
<211> LENGTH: 22
<212> TYPE: DNA
<213> ORGANISM: Artificial
<220> FEATURE:
<223> OTHER INFORMATION: Synthetic primer

<400> SEQUENCE: 7
caaaaggaag caactgtacc cc                                            22

<210> SEQ ID NO 8
<211> LENGTH: 14
<212> TYPE: DNA
<213> ORGANISM: Artificial
<220> FEATURE:
<223> OTHER INFORMATION: Synthetic primer

<400> SEQUENCE: 8
cttgctcgag atgt                                                     14

<210> SEQ ID NO 9
<211> LENGTH: 21
<212> TYPE: DNA
<213> ORGANISM: Artificial
<220> FEATURE:
```

```
<223> OTHER INFORMATION: Synthetic primer

<400> SEQUENCE: 9
gtctgcattg ttttgccagt g                                            21
```

METHODS FOR THE DIAGNOSIS OF GENITOURINARY CANCER

This application claims benefit of priority to U.S. Provisional Application Ser. No. 60/980,917, filed Oct. 18, 2007, the entire contents of which are hereby incorporated by reference.

BACKGROUND OF THE INVENTION

I. Field of the Invention

The invention relates to the fields of molecular and cellular biology, particularly to the use of antibodies to detect antigens diagnostic of genitourinay cancer in urine, semen or prostatic fluid.

II. Related Art

Bladder cancer is the fifth most common cancer in the United States accounting for about 4.6% of all cases (Jemal et al., 2007). Most incidences of bladder cancer are superficial and localized in character with about 74% of all cases being localized when diagnosed (Jemal et al., 2007). It exists in two main forms, non-invasive which lacks invasion into surrounding muscle tissue and is the more common form accounting for 75% of all cases and muscle invasive in which it spreads into surrounding urinary areas and may metastasize (Sengupta and Blute, 2006).

When diagnosed at early stages bladder cancer has about a 94% survival rate, but this rate drops dramatically to 46% when the cancer has spread to the surrounding region and to 6% when the cancer is distant at diagnosis (Jemal et al., 2007). Although most forms are non-invasive they have a large risk of recurrence after treatment (>50%) and high-grade superficial lesions carry a significant risk of progression (Sengupta and Blute, 2006).

The standard method of diagnosing bladder cancer is visualization by cystoscopy (Clark, 2007). However this technique is invasive, costly, and is limited by needing sight interpretations of growths (Sengupta and Blute, 2006). Inspection of cells in urine for abnormalities (urine cytology) and detection of chromosomal abnormalities in those cells (FISH or fluorescence in situ hybridization) are two other common methods of diagnosis without the invasiveness of cytology (Sengupta and Blute, 2006; Clark, 2007). However, urine cytology has very low sensitivity in detection of low grade disease (Sengupta and Blute, 2006; Clark, 2007) and FISH, while better at detecting low grade forms still carries low specificity and sensitivity and is subject to wide variation in effectiveness among cases (Clark, 2007).

More sensitive and specific early detection tools for bladder cancer and other genitourinary cancers would greatly improve patient survival. Also given the high recurrence rate, an easy follow up procedure that could be administered regularly would greatly improve treatment of recurrences. Urine, semen and prostatic fluid analysis, these fluids having come into close contact with genitourinary tissues, provides a tool unique to these kinds of cancer. Advantageously, such procedures are non-invasive and easy to administer. However, such techniques also require a marker of the disease that can be detected with high specificity and sensitivity in patients, which heretofore has not yet been identified.

SUMMARY OF THE INVENTION

Thus, in accordance with the present invention, there is provided a method of diagnosing genitourinary (GU) cancer in a subject comprising detecting elevated thromboxane receptor (TP) β, as compared to normal controls, in the urine, semen or prostatic fluid of the subject. Detecting may comprise immunologic detection, such as an ELISA or lateral flow assay. Detection may more specifically comprise exposing urine to a support comprising a first anti-TPβ antibody, and may further comprise exposing TPβ bound to the first anti-TPβ antibody to a second anti-TPβ antibody, the first and second anti-TPβ antibodies binding to different epitopes, such as where the second anti-TPβ antibody comprises a detectable label or where the second anti-TPβ is detected using an anti-Fc antibody that is labeled with a detectable marker. The support may be a membrane, a dipstick, a multi-well dish, a filter, a bead, or a biochip. The GU cancer may be bladder cancer, prostate cancer, urethral cancer or renal cancer, and the bladder cancer may be invasive, superficial or metastatic bladder cancer. The subject may previously have been diagnosed with, and successfully treated for, GU cancer.

In another embodiment, there is provided a method of monitoring the progression of GU cancer in a subject comprising assessing thromboxane receptor (TP) β level in the urine, semen or prostatic fluid of said subject at multiple time points, wherein an increase in TPβ level over time indicates progression of the GU cancer. Assessing may comprise immunologic detection, such as an ELISA or lateral flow assay. Assessing may more specifically comprise exposing urine to a support comprising a first anti-TPβ antibody, and may further comprise exposing TPβ bound to said first anti-TPβ antibody to a second anti-TPβ antibody, the first and second anti-TPβ antibodies binding to different epitopes, such as where the second anti-TPβ antibody comprises a detectable label or where the second anti-TPβ is detected using an anti-Fc antibody that is labeled with a detectable marker. The support may be a membrane, a dipstick, a multi-well dish, a filter, a bead, or a biochip. The GU cancer may be bladder cancer, prostate cancer, urethral cancer or renal cancer, and the bladder cancer may be invasive bladder cancer, superficial bladder cancer or metastatic bladder cancer. The multiple time points may be separated by at least one month, and/or the frequency of the time points may increase with time.

In yet another embodiment, there is provided a method of prognosing a GU cancer subject comprising assessing a thromboxane receptor (TP) β level in the urine, semen or prostatic fluid of said subject and comparing the level to a predetermined standard correlating with GU cancer stage. The GU cancer may be bladder cancer, prostate cancer, urethral cancer or renal cancer. Assessing may comprise immunologic detection, such as an ELISA or lateral flow assay. Assessing may more specifically comprise exposing urine to a support comprising a first anti-TPβ antibody, and may further comprise exposing TPβ bound to said first anti-TPβ antibody to a second anti-TPβ antibody, the first and second anti-TPβ antibodies binding to different epitopes, such as where the second anti-TPβ antibody comprises a detectable label or where the second anti-TPβ is detected using an anti-Fc antibody that is labeled with a detectable marker. The support may be a membrane, a dipstick, a multi-well dish, a filter, a bead, or a biochip.

In still yet another embodiment, there is provided a method of monitoring the treatment of GU cancer in a subject comprising assessing a thromboxane receptor (TP) β level in the urine, semen or prostatic fluid of said subject at multiple time points, wherein a decrease in TPβ level over time indicates treatment efficacy. The GU cancer may be bladder cancer, prostate cancer, urethral cancer or renal cancer. The method may further comprise altering a treatment based on the TPβ level. Assessing may comprise immunologic detection, such as an ELISA or lateral flow assay. Assessing may more specifically comprise exposing urine to a support comprising a first anti-TPβ antibody, and may further comprise exposing TPβ bound to said first anti-TPβ antibody to a second anti-TPβ antibody, the first and second anti-TPβ antibodies binding to different epitopes, such as where the second anti-TPβ antibody comprises a detectable label or where the second anti-TPβ is detected using an anti-Fc antibody that is labeled with a detectable marker. The support may be a membrane, a dipstick, a multi-well dish, a filter, a bead, or a biochip. The multiple time points may be separated by at least one month, and/or the frequency of the time points may increase with time.

In yet a further embodiment, there is provided a method of staging a genitourinary cancer in a subject comprising assessing a thromboxane receptor (TP) β level in the urine of the subject and comparing the level to a predetermined level for one or more given stages of a genitourinary cancer. The genitourinary cancer may be bladder cancer, prostate cancer, urethral cancer or renal cancer, and in a particular embodiment, the cancer is bladder cancer and the stage is Stage 0, I, II, III, IV, or recurrent. Assessing may comprise immunologic detection, such as an ELISA or lateral flow assay. Assessing may more specifically comprise exposing urine to a support comprising a first anti-TPβ antibody, and may further comprise exposing TPβ bound to said first anti-TPβ antibody to a second anti-TPβ antibody, the first and second anti-TPβ antibodies binding to different epitopes, such as where the second anti-TPβ antibody comprises a detectable label or where the second anti-TPβ is detected using an anti-Fc antibody that is labeled with a detectable marker. The support may be a membrane, a dipstick, a multi-well dish, a filter, a bead, or a biochip.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed.

(FIG. 1A) RNA was extracted from bladder tumor tissue and from adjacent normal tissue and cDNA was prepared from it. cDNA was then run in real time PCR with primers for the TPα. Expression levels shown are normalized to HPRT run on the same process. The difference in expression levels is not statistically significant (P=0.9). (FIG. 1B) With RNA extracted from the same tissue samples real time PCR was run with primers for TPβ and expression levels were normalized to HPRT. The difference in expression levels between the two tissue types is not statistically significant (P=0.3).

DETAILED DESCRIPTION OF THE INVENTION

Figure 1:
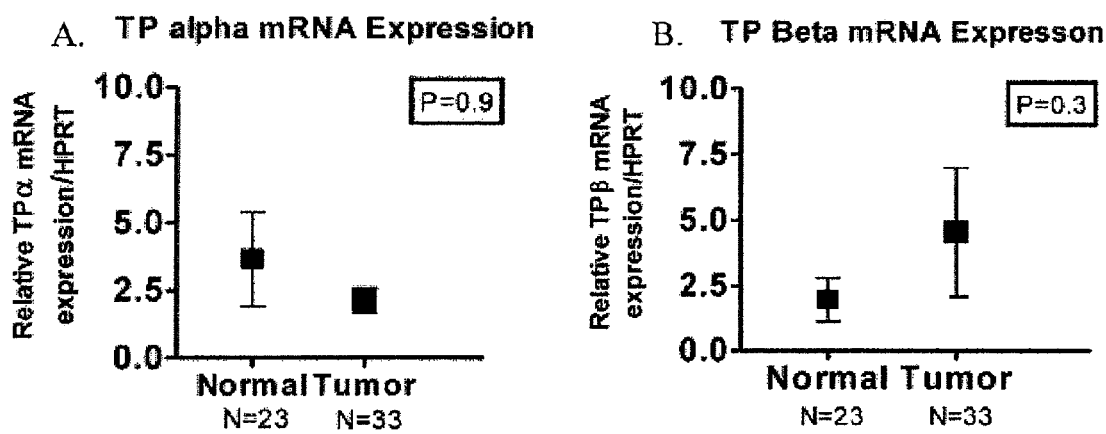
FIGS. 1A-B. Neither TPα or TPβ Is Over Expressed in Bladder Tumor Tissue Samples.

The inventors have evaluated the potential of TP receptor levels in urine as a diagnostic marker for bladder cancer, as well as other cancers. Bladder cancer tumors show overexpresson of TPβ on the protein level. TPα expression remains essentially unchanged on all levels. These relationships can be detected in urine samples of patients with bladder cancer as well. Urine samples taken from bladder cancer patients show elevated levels of TPβ protein, while TPα protein levels and mRNA levels of both so no elevations.

While the inventors previously showed that TP receptor protein was overexpressed in common types of bladder cancer (Moussa et al., 2005), here they report that it is in fact only the β isoform of the protein that has the link to bladder cancer. The α form remains unchanged and shows no role in bladder tumors. The overexpression of TPβ in bladder tumor identifies it as a marker of the disease and its potential importance in diagnosis.

The fact that urine sample analysis can detect the TPβ marker makes it a strong candidate for a diagnosis tool. The ELISA assay used strongly showed itself as a potential diagnostic tool. The small scale of the ELISA procedure makes it a perfect example of a bedside tool. Since the assay can confirm diagnosed patients it has a role as a routine screening tool. Potential early detection of bladder cancer would improve patient outlook as its use as a routine screen for recurrence would improve the outlook for the high recurrence rates of the disease. Further evaluation of the sensitivity and specificity of the assay is needed to further develop its role in diagnosis.

From other data, it appears that the role TPβ plays in tumor formation is not clear, but the results suggest a level for the action to occur. The TPβ marker appears on the protein level in tumors while the mRNA message level was shown not to change. The difference in TPβ for cancer then happens post-transcriptionally. Altered post-transcriptional control of the TPβ protein is involved in the mechanism of its tumor formation capabilities in bladder cancer. These findings offer urine, semen or prostatic fluid detection of the protein, though ELISA for example, for diagnosis of bladder cancer as well as other genitourinary cancers.

I. GENITOURINARY CANCERS

Genitourinary (GU) cancers are those cancers affecting organs of the body that help eliminate waste products, although not exclusively. Included within this group are cancers of the prostate, bladder, urethra, kidney (renal cell) and testicles. In 2007, it is estimated that nearly one out of four new cancers diagnosed in the United States will be a genitourinary (GU) malignancy (prostate, kidney, bladder/urethral or testicular cancer), and 10% of cancer deaths will result from GU cancers. Despite significant progress in molecular and cellular biology that has helped identify specific molecular pathways that contribute to the biological potential and behavior of GU cancers, current treatments for advanced prostate, kidney, urethral and bladder cancers remain limited.

A. Bladder Cancer i. General Background

Bladder cancer refers to any of several types of malignant growths of the urinary bladder, with over 65,000 new cases and some 13,750 attributed deaths reported in 2007 alone. It is a disease in which abnormal cells multiply without control in the bladder. The bladder is a hollow, muscular organ that stores urine; it is located in the pelvis. The most common type of bladder cancer begins in cells lining the inside of the bladder and is called urothelial cell or transitional cell carcinoma (UCC or TCC).

Bladder cancer characteristically causes blood in the urine, this may be visible to the naked eye (frank haematuria) or detectable only be microscope (microscopic haematuria). Other possible symptoms include pain during urination, frequent urination or feeling the need to urinate without results. These signs and symptoms are not specific to bladder cancer, and are also caused by non-cancerous conditions, including prostate infections and cystitis.

Exposure to environmental carcinogens of various types is responsible for the development of most bladder cancers. Tobacco use (specifically cigarette smoking) is thought to cause 50% of bladder cancers discovered in male patients and 30% of those found in female patients. Thirty percent of bladder tumors probably result from occupational exposure in the workplace to carcinogens such as benzidine. Occupations at risk are metal industry workers, rubber industry workers, workers in the textile industry and people who work in printing. Hairdressers are thought to be at risk as well because of their frequent exposure to permanent hair dyes. It has been proposed that hair dyes are a risk factor, and some have shown an odds ratio of 2.1 to 3.3 for risk of developing bladder cancer among women who use permanent hair yes, while others have shown no correlation between the use of hair dyes and bladder cancer. Certain drugs such as cyclophosphamide and phenacetin are known to predispose to bladder TCC. Chronic bladder irritation (infection, bladder stones, catheters, bilharzia) predisposes to squamous cell carcinoma of the bladder. Approximately 20% of bladder cancers occur in patients without predisposing risk factors. Bladder cancer is not currently believed to be heritable.

Like virtually all cancers, bladder cancer development involves the acquisition of mutations in various oncogenes and tumor supressor genes. Genes which may be altered in bladder cancer include FGFR3, HRAS, RB1 and P53. Several genes have been identified which play a role in regulating the cycle of cell division, preventing cells from dividing too rapidly or in an uncontrolled way. Alterations in these genes may help explain why some bladder cancers grow and spread more rapidly than others.

A family history of bladder cancer is also a risk factor for the disease. Many cancer experts assert that some people appear to inherit reduced ability to break down certain chemicals, which makes them more sensitive to the cancer-causing effects of tobacco smoke and certain industrial chemicals.

ii. Traditional Diagnosis

The gold standard of diagnosing bladder cancer is urine cytology and transurethral (through the urethra) cystoscopy. Urine cytology can be obtained in voided urine or at the time of the cystoscopy ("bladder washing"). Cytology is very specific (a positive result is highly indicative of bladder cancer) but suffers from low sensitivity (a negative result does not exclude the diagnosis of cancer). There are newer urine bound markers for the diagnosis of bladder cancer. These markers are more sensitive but not as specific as urine cytology. They are much more expensive as well. Many patients with a history, signs, and symptoms suspicious for bladder cancer are referred to a urologist or other physician trained in cystoscopy, a procedure in which a flexible tube bearing a camera and various instruments is introduced into the bladder through the urethra. Suspicious lesions may be biopsied and sent for pathologic analysis.

Ninety percent of bladder cancer are transitional cell carcinomas (TCC) that arise from the inner lining of the bladder called the urothelium. The other 10% of tumours are squamous cell carcinoma, adenocarcinoma, sarcoma, small cell carcinoma and secondary deposits from cancers elsewhere in the body.

TCCs are often multifocal, with 30-40% of patients having a more than one tumour at diagnosis. The pattern of growth of TCCs can be papillary, sessile (flat) or carcinoma-in-situ (CIS). The 1973 WHO grading system for TCCs (papilloma, G1, G2 or G3) is most commonly used despite being superseded by the 2004 WHO grading (papillary neoplasm of low malignant potential (PNLMP), low grade and high grade papillary carcinoma. CIS invariably consists of cytologically high grade tumour cells.

Bladder TCC is staged according to the 1997 TNM system:

Ta—non-invasive papillary tumour

T1—invasive but not as far as the muscular bladder layer

T2—invasive into the muscular layer

T3—invasive beyond the muscle into the fat outside the bladder

T4—invasive into surrounding structures like the prostate, uterus or pelvic wall The following stages are used to classify the location, size, and spread of the cancer, according to the TNM (tumor, lymph node, and metastases) staging system:

Stage 0: Cancer cells are found only on the inner lining of the bladder.

Stage I: Cancer cells have proliferated to the layer beyond the inner lining of the urinary bladder but not to the muscles of the urinary bladder.

Stage II: Cancer cells have proliferated to the muscles in the bladder wall but not to the fatty tissue that surrounds the urinary bladder.

Stage III: Cancer cells have proliferated to the fatty tissue surrounding the urinary bladder and to the prostate gland, vagina, or uterus, but not to the lymph nodes or other organs.

Stage IV: Cancer cells have proliferated to the lymph nodes, pelvic or abdominal wall, and/or other organs.

Recurrent: Cancer has recurred in the urinary bladder or in another nearby organ after having been treated.

B. Renal Cancer i. General Background

Renal cell carcinoma is the most common form of kidney cancer arising from the renal tubule. It is the most common type of kidney cancer in adults. Initial treatment is surgery. It is notoriously resistant to radiation therapy and chemotherapy, although some cases respond to immunotherapy. The advent of targeted cancer therapies such as Sunitinib has vastly improved the outlook for treatment of RCC.

Renal cell carcinoma affects about three in 10,000 people, resulting in about 31,000 new cases in the US per year. Every year, about 12,000 people in the US die from renal cell carcinoma. It is more common in men than women, usually affecting men older than 55. Why the cells become cancerous is not known. A history of smoking greatly increases the risk for developing renal cell carcinoma. Some people may also have inherited an increased risk to develop renal cell carcinoma, and a family history of kidney cancer increases the risk. People with von Hippel-Lindau disease, a hereditary disease that also affects the capillaries of the brain, commonly also develop renal cell carcinoma. Kidney disorders that require dialysis for treatment also increase the risk for developing renal cell carcinoma.

ii. Traditional Diagnosis

The characteristic appearance of renal cell carcinoma (RCC) is a solid renal lesion which disturbs the renal contour. It will frequently have an irregular or lobulated margin. 85% of solid renal masses will be RCC. Ten percent of RCC will contain calcifications, and some contain macroscopic fat (likely due to invasion and encasement of the perirenal fat). Following intravenous contrast administration (computed tomography or magnetic resonance imaging), enhancement will be noted, and will increase the conspicuity of the tumor relative to normal renal parenchyma.

A list of solid renal lesions includes renal cell carcinoma, metastasis from an extra-renal primary neoplasm, renal lymphoma, squamous cell carcinoma, juxtaglomerular tumor (reninoma), transitional cell carcinoma, angiomyolipoma, oncocytoma and Wilm's tumor. In particular, reliably distinguishing renal cell carcinoma from an oncocytoma (a benign lesion) is not possible using current medical imaging or percutaneous biopsy.

Renal cell carcinoma may also be cystic. As there are several benign cystic renal lesions (simple renal cyst, hemorrhagic renal cyst, multilocular cystic nephroma, polycystic kidney disease), it may occasionally be difficult for the radiologist to differentiate a benign cystic lesion from a malignant one. Bosniak developed a classification system for cystic renal lesions that classifies them based specific imaging features into groups that are benign and those that need surgical resection. At diagnosis, 30% of renal cell carcinoma has spread to that kidney's renal vein, and 5-10% has continued on into the inferior vena cava.

Percutaneous biopsy can be performed by a radiologist using ultrasound or computed tomography to guide sampling of the tumor for the purpose of diagnosis. However this is not routinely performed because when the typical imaging features of renal cell carcinoma are present, the possibility of an incorrectly negative result together with the risk of a medical complication to the patient make it unfavorable from a risk-benefit perspective. This is not completely accurate, there are new experimental treatments.

C. Prostate Cancer i. General Background

Prostate cancer is a disease in which cancer develops in the prostate, a gland in the male reproductive system. In 2007, almost 220,000 new cases were reported, and over 27,000 deaths were attributed to this malignancy. It occurs when cells of the prostate mutate and begin to multiply out of control. These cells may spread (metastasize) from the prostate to other parts of the body, especially the bones and lymph nodes. Prostate cancer may cause pain, difficulty in urinating, erectile dysfunction and other symptoms.

Rates of prostate cancer vary widely across the world. Although the rates vary widely between countries, it is least common in South and East Asia, more common in Europe, and most common in the United States. According to the American Cancer Society, prostate cancer is least common among Asian men and most common among black men, with figures for white men in-between. However, these high rates may be affected by increasing rates of detection.

Prostate cancer develops most frequently in men over fifty. This cancer can occur only in men, as the prostate is exclusively of the male reproductive tract. It is the most common type of cancer in men in the United States, where it is responsible for more male deaths than any other cancer, except lung cancer. However, many men who develop prostate cancer never have symptoms, undergo no therapy, and eventually die of other causes. Many factors, including genetics and diet, have been implicated in the development of prostate cancer.

ii. Traditional Diagnosis

Prostate cancer screening is an attempt to find unsuspected cancers. Screening tests may lead to more specific follow-up tests such as a biopsy, where small pieces of the prostate are removed for closer study. As of 2006 prostate cancer screening options include the digital rectal exam and the prostate specific antigen (PSA) blood test. Screening for prostate cancer is controversial because it is not clear if the benefits of screening outweigh the risks of follow-up diagnostic tests and cancer treatments.

Prostate cancer is a slow-growing cancer, very common among older men. In fact, most prostate cancers never grow to the point where they cause symptoms, and most men with prostate cancer die of other causes before prostate cancer has an impact on their lives. The PSA screening test may detect these small cancers that would never become life threatening. Doing the PSA test in these men may lead to overdiagnosis, including additional testing and treatment. Follow-up tests, such as prostate biopsy, may cause pain, bleeding and infection. Prostate cancer treatments may cause urinary incontinence and erectile dysfunction. Therefore, it is essential that the risks and benefits of diagnostic procedures and treatment be carefully considered before PSA screening.

Prostate cancer screening generally begins after age 50, but this can vary due to ethnic backgrounds. Thus, the American Academy of Family Physicians and American College of Physicians recommend the physician discuss the risks and benefits of screening and decide based on individual patient preference. Although there is no officially recommended cut-off, many health care providers stop monitoring PSA in men who are older than 75 years old because of concern that prostate cancer therapy may do more harm than good as age progresses and life expectancy decreases.

Digital rectal examination (DRE) is a procedure where the examiner inserts a gloved, lubricated finger into the rectum to check the size, shape, and texture of the prostate. Areas which are irregular, hard or lumpy need further evaluation, since they may contain cancer. Although the DRE only evaluates the back of the prostate, 85% of prostate cancers arise in this part of the prostate. Prostate cancer which can be felt on DRE is generally more advanced. The use of DRE has never been shown to prevent prostate cancer deaths when used as the only screening test.

The PSA test measures the blood level of prostate-specific antigen, an enzyme produced by the prostate. Specifically, PSA is a serine protease similar to kallikrein. Its normal function is to liquify gelatinous semen after ejaculation, allowing spermatazoa to more easily navigate through the uterine cervix.

PSA levels under 4 ng/mL (nanograms per milliliter) are generally considered normal, however in individuals below the age of 50 sometimes a cutoff of 2.5 is used for the upper limit of normal, while levels over 4 ng/mL are considered abnormal (although in men over 65 levels up to 6.5 ng/mL may be acceptable, depending upon each laboratory's reference ranges). PSA levels between 4 and 10 ng/mL indicate a risk of prostate cancer higher than normal, but the risk does not seem to rise within this six-point range. When the PSA level is above 10 ng/mL, the association with cancer becomes stronger. However, PSA is not a perfect test. Some men with prostate cancer do not have an elevated PSA, and most men with an elevated PSA do not have prostate cancer.

PSA levels can change for many reasons other than cancer. Two common causes of high PSA levels are enlargement of the prostate (benign prostatic hypertrophy (BPH)) and infection in the prostate (prostatitis). It can also be raised for 24 hours after ejaculation and several days after catheterization. PSA levels are lowered in men who use medications used to treat BPH or baldness. These medications, finasteride (marketed as Proscar or Propecia) and dutasteride (marketed as Avodart), may decrease the PSA levels by 50% or more.

Several other ways of evaluating the PSA have been developed to avoid the shortcomings of simple PSA screening. The use of age-specific reference ranges improves the sensitivity and specificity of the test. The rate of rise of the PSA over time, called the PSA velocity, has been used to evaluate men with PSA levels between 4 and 10 ng/ml, but as of 2006, it has not proven to be an effective screening test. Comparing the PSA level with the size of the prostate, as measured by ultrasound or magnetic resonance imaging, has also been studied. This comparison, called PSA density, is both costly and, as of 2006, has not proven to be an effective screening test. PSA in the blood may either be free or bound to other proteins. Measuring the amount of PSA which is free or bound may provide additional screening information, but as of 2006, questions regarding the usefulness of these measurements limit their widespread use.

When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

If cancer is suspected, a biopsy is offered. During a biopsy a urologist obtains tissue samples from the prostate via the rectum. A biopsy gun inserts and removes special hollow-core needles (usually three to six on each side of the prostate) in less than a second. Prostate biopsies are routinely done on an outpatient basis and rarely require hospitalization. Fifty-five percent of men report discomfort during prostate biopsy.

The tissue samples are then examined under a microscope to determine whether cancer cells are present, and to evaluate the microscopic features of any cancer found. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastisis—opposite to what is found in many other cancers that metastisize.

D. Urethral Cancer i. General Background

The urethra is the tube that carries urine from the bladder to outside the body. In women, the urethra is about 1½ inches long and is just above the vagina. In men, the urethra is about 8 inches long, and goes through the prostate gland and the penis to the outside of the body. In men, the urethra also carries semen. Urethral cancer is a rare cancer that occurs more often in women than in men. There are different types of urethral cancer that begin in cells that line the urethra. Squamous cell carcinoma is the most common type of urethral cancer. It forms in cells in the part of the urethra near the bladder in women, and in the lining of the urethra in the penis in men. Transitional cell carcinoma forms in the area near the urethral opening in women, and in the part of the urethra that goes through the prostate gland in men. Adenocarcinoma forms in glands near the urethra in both men and women.

Urethral cancer can metastasize quickly to tissues around the urethra and is often found in nearby lymph nodes by the time it is diagnosed. Age and a history of bladder cancer can affect the risk of developing urethral cancer, as well as having a history of bladder cancer, having conditions that cause chronic inflammation in the urethra, including sexually transmitted diseases (STDs), frequent urinary tract infections (UTIs), being 60 or older, and being a white female. Possible signs of urethral cancer include bleeding or trouble with urination (weak flow, frequent urination, discharge), or a lump or thickness in the perineum or penis or lymph nodes in the groin area.

Certain factors affect prognosis and treatment options. The prognosis depends on the stage and size of the cancer, where in the urethra the cancer first formed, the patient's general health, and whether the cancer has just been diagnosed or has recurred. Treatment options depend on the stage of the cancer and where it is in the urethra, the patient's sex and general health and whether the cancer has just been diagnosed or has recurred.

ii. Traditional Diagnosis

Tests that examine the urethra and bladder are used to detect (find) and diagnose urethral cancer. The following tests and procedures may be used.

Physical exam and history. An exam of the body to check general signs of health, including checking for signs of disease, such as lumps or anything else that seems unusual. A history of the patient's health habits and past illnesses and treatments will also be taken.

Laboratory tests. Medical procedures that test samples of tissue, blood, urine, or other substances in the body. These tests help to diagnose disease, plan and check treatment, or monitor the disease over time.

Urine cytology. Examination of urine under a microscope to check for abnormal cells.

Urinalysis. A test to check the color of urine and its contents, such as sugar, protein, blood, and white blood cells. If white blood cells (a sign of infection) are found, a urine culture is usually done to find out what type of infection it is.

Digital rectal exam. An exam of the rectum. The doctor or nurse inserts a lubricated, gloved finger into the lower part of the rectum to feel for lumps or anything else that seems unusual. This procedure may be done while the patient is under anesthesia.

Pelvic exam. An exam of the vagina, cervix, uterus, fallopian tubes, ovaries, and rectum. The doctor or nurse inserts one or two lubricated, gloved fingers of one hand into the vagina and places the other hand over the lower abdomen to feel the size, shape, and position of the uterus and ovaries. A speculum is also inserted into the vagina and the doctor or nurse looks at the vagina and cervix for signs of disease. This may be done while the patient is under anesthesia.

Cystoscopy. A procedure to look inside the urethra and bladder to check for abnormal areas. A cystoscope (a thin, lighted tube) is inserted through the urethra into the bladder. Tissue samples may be taken for biopsy.

Biopsy. The removal of cells or tissues from the urethra, bladder, and, sometimes, the prostate gland, so they can be viewed under a microscope by a pathologist to check for signs of cancer.

II. THROMBOXANE RECEPTORS

A. Thromboxane Receptor Function

Thromboxane is intermediate in the metabolism of arachidonic acid via the COX pathway (Jabbour et al., 2006). After being made, it binds to thromboxane (TP) receptors which are G-protein coupled receptors (GPCRs) that have been shown to have a number of complex downstream signaling effects; although they are not fully understood and differ among cell types (Jabbour et al., 2006; Huang et al., 2004). The thromboxane receptor is found on the surface of cells in the endothelium of blood vessels and in the placenta which interacts with the eicosanoid lipid thromboxane. The TP GPCR has been implicated in a number of signaling effects such as platelet activation, smooth muscle contraction, and responses caused by the central and peripheral nervous system (Jabbour et al., 2006; Huang et al., 2004). Thromboxane is a potent stimulator for platelet aggregation and clot formation and also plays a role in vascular tone. Mutation of the receptor can lead to a bleeding disorder.

The gene responsible for the thromboxane receptor, TBXA2R is found on chromosome 19 and spans 15 kilobases.

B. β Isoform

It was discovered that TP receptors exist in two isoforms: TPα and TPβ that differed in the amino acid sequence of their C-terminal tails which reside in the cytoplasm (Valentin et al., 2005). The α and β forms are differential regulated and under the control of 2 distinct promoters letting them have a wide variety of effects in a number of cell types (Coyle and Kinsella, 2005). The reason for and the effects of these two splices variants in humans is not understood (Valentin et al., 2005; Coyle and Kinsella, 2005).

The inventors have previously showed that the TP receptor is overexpressed in tissue of the most common forms of bladder cancer on the protein level, but not the mRNA level (Moussa et al., 2005). This first indicated TP receptor as a biomarker of bladder cancer. Further study by this inventors' laboratories has suggested that it is TPβ that is being overexpressed in relation to TPα in common bladder tumor tissue samples. Based on this, it is hypothesized that TPβ protein detection could provide a new diagnostic tool in urine sample analysis. The detection of TPβ overexpression at low levels in patient urine samples provides a non-invasive early diagnosis method and easy technique for follow up detection of recurrence.

C. Sequences

The nucleic acid and amino acid sequences for TPα and TPβ are found in the sequence listing as SEQ ID NOS:1-2 (NM_001060; NP_001051) and 3-4 (NM 201636; NP_963998), respectively.

III. DIAGNOSTICS

According to the inventors' findings, detection of abnormal levels of TPβ is diagnostic of genitourinary (GU) cancer, and the protein can be found in diagnostically significant levels in urine, semen and prostatic fluid. As a consequence, testing for the presence of this protein in these fluids could be an early diagnostic method for GU cancers. The convenience of this form of identification will permit frequent testing and therefore early diagnosis, with the goal of earlier intervention and limiting or cure of otherwise life-threatening disease. In addition, one may monitor disease and/or treatment progression in GU cancer patients.

A commercial source for anti-TPβ is Genway Biotech (San Diego, Calif.), cat. no. 18-461-10350.

A. Preparing Antibodies

Methods for the production of antibodies are well known in the art, as described in see, e.g., Harlow and Lane, 1988; U.S. Pat. No. 4,196,265. The methods for generating monoclonal antibodies (MAbs) generally begin along the same lines as those for preparing polyclonal antibodies. The first step for both these methods is immunization of an appropriate host. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Various methods may be employed for the cloning an expression of human light and heavy chain sequences. Wardemann et al. (2003) and Takekoshi et al. (2001), both of which disclose such techniques, are hereby incorporated by reference.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations; and U.S. Pat. No. 4,867,973 which describes antibody-therapeutic agent conjugates.

B. Immunologic Assays

Antibodies of the present invention can be used in characterizing the TPβ content of urine, prostate fluid and semen through techniques such as RIAs, ELISAs and Western blotting. This provides early detection and monitoring of bladder cancer, possibly prior to tissue invasion and metastasis.

Immunoassays can be classified according to the assay type, assay method and endpoint labeling method. These three major criteria for classification that have the greatest influence on the performance of test are, i) the use of a limited (type II) or excessive reagent format (type I), ii) the use of a homogeneous and heterogeneous format, iii) the use of a label or unlabelled assay format and the choice of label. The present invention contemplates the use of all these kinds of immunoassays.

Type I assay. In Type I assay format, where antigen binds to an excess of antibody, the most common method is sandwich assay. In this approach, the first antibody (capture Ab) in excess is coupled to a solid phase. The bound antigen is then detected with a second antibody (indicator Ab) labeled with various indicators such as enzymes, fluorophores, radioisotopes, particles, etc. In this assay, the amount of indicator antibody captured on the solid phase is directory proportional to the amount of antigen in the sample.

In the present invention, an ELISA assay is particularly contemplated. For example, antibodies to TPβ may be immobilized onto a selected surface, for example, a surface such as a microtiter well, a membrane, a filter, a bead or a dipstick. After washing to remove incompletely adsorbed material, it is desirable to bind or coat the surface with a non-specific agent that is known to be antigenically neutral with regard to the test sample, e.g., bovine serum albumin (BSA), casein or solutions of powdered milk. This allows for blocking of non-specific adsorption sites on the immobilizing surface and thus reduces the background caused by non-specific binding of antibody to antigen on the surface.

After binding of antibody to the surface and coating, the surface is exposed to urine, prostate fluid or semen. Following formation of specific immunocomplexes between antigens in the urine, prostate fluid or semen and the antibody, and subsequent washing, the occurrence and even amount of immunocomplex formation may be determined by subjecting the same to a second antibody having specificity for the antigen. Appropriate conditions preferably include diluting the sample with diluents such as BSA, bovine gamma globulin (BGG) and phosphate buffered saline (PBS)/Tween®. These added agents also tend to assist in the reduction of non-specific background. The detecting antibody is then allowed to incubate for from about 2 to about 4 hr, at temperatures preferably on the order of about 25° to about 27° C. Following incubation, the surface is washed so as to remove non-immunocomplexed material. A preferred washing procedure includes washing with a solution such as PBS/Tween®, or borate buffer.

To provide a detecting means, the second antibody will preferably have an associated label, e.g., an enzyme that will generate a color development upon incubating with an appropriate chromogenic substrate. Thus, for example, one will desire to contact and incubate the second antibody for a period of time and under conditions which favor the development of immunocomplex formation (e.g., incubation for 2 hr at room temperature in a PBS-containing solution such as PBS/Tween®).

After incubation with the second antibody, and subsequent to washing to remove unbound material, the amount of label is quantified (e.g., by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label). Quantitation is then achieved by measuring the label, e.g., degree of color generation, e.g., using a visible spectrum spectrophotometer. Other potential labels include radiolabels, fluorescent labels, dyes and chemiluminescent molecules (e.g., luciferase).

Type II assay. In Type II assay formats, a limited amount of antibody is used (insufficient to bind the entire antigen) a prefixed amount of labeled antigen competes with the unlabeled antigen in test sample for a limited number of antibody binding sites. The concentration of unlabeled antigen in specimen can be determined from the portion of labeled antigen that is bound to the antibody. Since most analyte molecules are not enough large to provide two different epitopes in this method, the response will be inversely proportional to the concentration of antigen in the unknown.

Homogenous and Heterogenous Assay. The use off either competitive or immunometric assays requires differention of bound from free label. This can be archived either by separating bound from free label using a means of removing antibody (heterogeneous) or mo dulation of signal of the label when antigen is bound to antibody cpmapred to when it is free (homogeneous).

Most solid phase immunoassays belong to the Heterogeneous Assay category. There are many ways of separating bound from free label such as precipitation of antibody, chromatographic method, and solid phase coupling antibody. Homogeneous assays do not require any of separation step to distinguish antigen bound antibody from free antibody. It has an advantage in automation, and typically is faster, easier to perform, and more cost-effective, but its specificity and sensitivity are lower.

Immunochromatography. There is two different immunochromatography assays based on porous materials—nitrocellulose or nylon membrane. Depending on the liquid migration method, these are classified as lateral flow assay (LFA) or flow through assay (FTA). LFA methods are described in U.S. Pat. No. 6,485,982 is original patent belong to IMA C. Dipstick Technology U.S. Pat. No. 4,366,241, and Zuk, EP-A 0 143 574 describe migration type assays in which a membrane is impregnated with the reagents needed to perform the assay. An analyte detection zone is provided in which labeled analyte is bound and assay indicia is read.

U.S. Pat. No. 4,770,853, WO 88/08534, and EP-A 0 299 428 describe migration assay devices which incorporate within them reagents which have been attached to colored direct labels, thereby permitting visible detection of the assay results without addition of further substances.

U.S. Pat. No. 4,632,901, disclose a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

EP-A 0 125 118, disclose a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution.

EP-A 0 282 192, disclose a dipstick device for use in competition type assays.

U.S. Pat. No. 4,313,734 describes the use of gold sol particles as a direct label in a dipstick device.

U.S. Pat. No. 4,786,589 describes a dipstick immunoassay device in which the antibodies have been labeled with formazan.

U.S. Pat. No. 5,656,448 pertains to dipstick immunoassay devices comprising a base member and a single, combined sample contact zone and test zone, wherein the test zone incorporates the use of symbols to detect analytes in a sample of biological fluid. A first immunological component, an anti-immunoglobulin capable of binding to an enzyme-labeled antibody, is immobilized in a control indicator portion. A second immunological component, capable of specifically binding to a target analyte which is bound to the enzyme-labeled antibody to form a sandwich complex, is immobilized in a test indicia portion. The enzyme-labeled antibody produces a visual color differential between a control indicia portion and a non-indicia portion in the test zone upon contact with a substrate. The device additionally includes a first polyol and a color differential enhancing component selected from the group consisting of an inhibitor to the enzyme and a competitive secondary substrate for the enzyme distributed throughout the non-indicia portion of the test zone.

D. Kits

In still further embodiments, the present invention concerns immunodetection kits for use with the immunodetection methods described above. The kits will include antibodies to TPβ, and may contain other reagents as well. The immunodetection kits will thus comprise, in suitable container means, a first antibody that binds to TPβ, and optionally a second and distinct antibody to TPβ.

In certain embodiments, the antibody to TPβ may be prebound to a solid support, such as a column matrix, a microtitre plate, a filter, a membrane, a bead or a dipstick. The immunodetection reagents of the kit may take any one of a variety of forms, including antibodies to TPβ containing detectable labels. As noted above, a number of exemplary labels are known in the art and all such labels may be employed in connection with the present invention.

The kits may further comprise a suitably aliquoted composition of TPβ, whether labeled or unlabeled, as may be used to prepare a standard curve for a detection assay. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

IV. TREATMENTS

A. Bladder Cancer

The treatment of bladder cancer depends on how deep the tumor invades into the bladder wall. Superficial tumors (those not entering the muscle layer) can be "shaved off" using an electrocautery device attached to a cystoscope.

Immunotherapy in the form of BCG instillation is also used to treat and prevent the recurrence of superficial tumors. BCG immunotherapy is effective in up to ⅔ of the cases at this stage. Instillations of chemotherapy into the bladder can also be used to treat superficial disease. *Bacillus* Calmette-Guerin (BCG) has been in use since the 1980's, and is the most proven and effective form of immunotherapy at this point in time. BCG is an inactivated form of the bacterium *Mycobacterium tuberculosis*, which is given both intravesically mixed in a saline solution and instilled directly into the bladder via a catheter, as well as in the form of a percutaneous vaccine. Although it is not yet totally understood why BCG and other immunotherapies work against cancer, they are thought to elicit an immune response.

It has been shown that BCG induces a variety of cytokines into the urine of patients with superficial TCC, and that some cytokines have antiangiogenic activity. One study demonstrated that interferon-inducible protein 10 (IP-10) and its inducing anti-angiogenic cytokines, interferon-γ and interleukin-12, are increased during intravesical BCG immunotherapy of bladder TCC. These data suggest that, in addition to a cellular immune response, BCG may induce a cytokine-mediated antiangiogenic environment that aids in inhibiting future tumor growth and progression.

Though side effects vary with the individual, the great majority of people find BCG treatments tolerable with side effects being temporary, and some have no adverse reactions at all. Dysuria (pain or difficulty upon urination) and urinary frequency are expected as a consequence of the inflammatory response, and cystitis is the most frequent adverse reaction-occurring in up to 90% of cases. Blood in the urine may occur with cystitis and is seen in one-third of patients. Irritative bladder symptoms are unlikely in the week after the first intravesical BCG. Side effects of BCG are cumulatory, and generally increase with successive treatments. Some people complain of flu like symptoms including fatigue, joint pain and muscle ache.

Untreated, superficial tumors may gradually begin to infiltrate the muscular wall of the bladder. Tumors that infiltrate the bladder require more radical surgery where part or all of the bladder is removed (a cystectomy) and the urinary stream is diverted. In some cases, skilled surgeons can create a substitute bladder (a neobladder) from a segment of intestinal tissue, but this largely depends upon patient preference, age of patient, renal function, and the site of the disease.

A combination of radiation and chemotherapy can also be used to treat invasive disease. It has not yet been determined how the effectiveness of this form of treatment compares to that of radical ablative surgery. There is weak observational evidence from one small study to suggest that the concurrent use of statins is associated with failure of BCG immunotherapy.

B. Renal Cancer

If only the kidneys are involved, which is about 40% of cases, it can be cured roughly 90% of the time with surgery. If it has spread outside of the kidneys, often into the lymph nodes or the main vein of the kidney, then it must be treated with chemotherapy and other treatments.

Surgical removal of all or part of the kidney (nephrectomy) is recommended. This may include removal of the adrenal gland, retroperitoneal lymph nodes, and possibly tissues involved by direct extension (invasion) of the tumor into the surrounding tissues. In cases where the tumor has spread into the renal vein, inferior vena cava, and possibly the right atrium (angioinvasion), this portion of the tumor can be surgically removed, as well. In case of metastases surgical resection of the kidney ("cytoreductive nephrectomy") may improve survival, as well as resection of a solitary metastatic lesion.

Percutaneous, image-guided therapies, usually managed by radiologists, are being offered to patients with localized tumor, but who are not good candidates for a surgical procedure. This sort of procedure involves placing a probe through the skin and into the tumor using real-time imaging of both the probe tip and the tumor by computed tomography, ultrasound, or even magnetic resonance imaging guidance, and then destroying the tumor with heat (radiofrequency ablation) or cold (cryotherapy). These modalities are at a disadvantage compared to traditional surgery in that pathologic confirmation of complete tumor destruction is not possible.

Radiation therapy is not commonly used for treatment of renal cell carcinoma because it is usually not successful. Radiation therapy may be used to palliate the symptoms of skeletal metastases.

Medications such as α-interferon and interleukin-2 (IL-2) have been successful in reducing the growth of some renal cell carcinomas, including some with metastasis. Studies have demonstrated that IL-2 offers the possibility of a complete and long-lasting remission in these diseases. In addition, the anti-VEGF monoclonal antibody bevacizumab has been shown to be promising in advanced disease.

Sorafenib (Nexavar) was FDA approved in December 2005 for treatment of advanced renal cell cancer, the first receptor tyrosine kinase (RTK) inhibitor indicated for this use.

A month later, Sunitinib (Sutent) was approved as well. Sunitinib—an oral, small-molecule, multi-targeted (RTK) inhibitor—and sorafenib both interfere with tumor growth by inhibiting angiogenesis as well as tumor cell proliferation. Sunitinib appears to offer greater potency against advanced RCC, perhaps because it inhibits more receptors than sorafenib. However, these agents have not been directly compared against one another in a single trial.

Temsirolimus (CCI-779) is an inhibitor of mTOR kinase (mammalian target of rapamycin) that was shown to prolong overall survival vs. interferon-α2b in patients with previously untreated metastatic renal cell carcinoma with three or more poor prognostic features.

Chemotherapy may be used in some cases, but cure is unlikely unless all the cancer can be removed with surgery.

In November 2006, it was announced that a vaccine had been developed and tested with very promising results. The new vaccine, called TroVax, works by harnessing the patient's own immune system to fight the disease.

C. Prostate Cancer

Prostate cancer can be treated with surgery, radiation therapy, hormonal therapy, occasionally chemotherapy, proton therapy, or some combination of these. The age and underlying health of the man as well as the extent of spread, appearance under the microscope, and response of the cancer to initial treatment are important in determining the outcome of the disease. Since prostate cancer is a disease of older men, many will die of other causes before a slowly advancing prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life.

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.). Most men who choose watchful waiting for early stage tumors eventually have signs of tumor progression, and they may need to begin treatment within three years. Although men who choose watchful waiting avoid the risks of surgery and radiation, the risk of metastasis (spread of the cancer) may be increased. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy.

Clinically insignificant prostate tumors are often found by accident when a doctor incorrectly orders a biopsy not following the recommended guidelines (abnormal DRE and elevated PSA). The urologist must check that the PSA is not elevated for other reasons, prostatitis, etc. An annual biopsy is often recommended by a urologist for a patient who has selected watchful waiting when the tumor is clinically insignificant (no abnormal DRE or PSA). The tumors tiny size can be monitored this way and the patient can decide to have surgery only if the tumor enlarges which may take many years or never.

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radical prostatectomy is effective for tumors which have not spread beyond the prostate; cure rates depend on risk factors such as PSA level and Gleason grade. However, it may cause nerve damage that significantly alters the quality of life of the prostate cancer survivor. The most common serious complications are loss of urinary control and impotence. Reported rates of both complications vary widely depending on how they are assessed, by whom, and how long after surgery, as well as the setting (e.g., academic series vs. community-based or population-based data). Although penile sensation and the ability to achieve orgasm usually remain intact, erection and ejaculation are often impaired. Medications such as sildenafil (Viagra), tadalafil (Cialis), or vardenafil (Levitra) may restore some degree of potency. For most men with organ-confined disease, a more limited "nerve-sparing" technique may help avoid urinary incontinence and impotence.

Radical prostatectomy has traditionally been used alone when the cancer is small. In the event of positive margins or locally advanced disease found on pathology, adjuvant radiation therapy may offer improved survival. Surgery may also be offered when a cancer is not responding to radiation therapy. However, because radiation therapy causes tissue changes, prostatectomy after radiation has a higher risk of complications.

Transurethral resection of the prostate, commonly called a "TURP," is a surgical procedure performed when the tube from the bladder to the penis (urethra) is blocked by prostate enlargement. TURP is generally for benign disease and is not meant as definitive treatment for prostate cancer. During a TURP, a small tube (cystoscope) is placed into the penis and the blocking prostate is cut away.

In metastatic disease, where cancer has spread beyond the prostate, removal of the testicles (called orchiectomy) may be done to decrease testosterone levels and control cancer growth.

Radiation therapy, also known as radiotherapy, uses ionizing radiation to kill prostate cancer cells. When absorbed in tissue, ionizing radiation such as γ and x-rays damage the DNA in cells, which increases the probability of apoptosis. Two different kinds of radiation therapy are used in prostate cancer treatment: external beam radiation therapy and brachytherapy.

External beam radiation therapy uses a linear accelerator to produce high-energy x-rays which are directed in a beam towards the prostate. A technique called Intensity Modulated Radiation Therapy (IMRT) may be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center. New types of radiation therapy may have fewer side effects then traditional treatment, one of these is Tomotherapy.

Permanent implant brachytherapy is a popular treatment choice for patients with low to intermediate risk features, can be performed on an outpatient basis, and is associated with good 10-year outcomes with relatively low morbidity. It involves the placement of about 100 small "seeds" containing radioactive material (such as iodine$^{125}$ or palladium$^{103}$) with a needle through the skin of the perineum directly into the tumor while under spinal or general anesthetic. These seeds emit lower-energy X-rays which are only able to travel a short distance. Although the seeds eventually become inert, they remain in the prostate permanently. The risk of exposure to others from men with implanted seeds is generally accepted to be insignificant.

Radiation therapy is commonly used in prostate cancer treatment. It may be used instead of surgery for early cancers, and it may also be used in advanced stages of prostate cancer to treat painful bone metastases. Radiation treatments also can be combined with hormonal therapy for intermediate risk disease, when radiation therapy alone is less likely to cure the cancer. Some radiation oncologists combine external beam radiation and brachytherapy for intermediate to high risk situations. One study found that the combination of six months of androgen suppressive therapy combined with external beam radiation had improved survival compared to radiation alone in patients with localized prostate cancer. Others use a "triple modality" combination of external beam radiation therapy, brachytherapy, and hormonal therapy.

Less common applications for radiotherapy are when cancer is compressing the spinal cord, or sometimes after surgery, such as when cancer is found in the seminal vesicles, in the lymph nodes, outside the prostate capsule, or at the margins of the biopsy.

Radiation therapy is often offered to men whose medical problems make surgery more risky. Radiation therapy appears to cure small tumors that are confined to the prostate just about as well as surgery. However, as of 2006 some issues remain unresolved, such as whether radiation should be given to the rest of the pelvis, how much the absorbed dose should be, and whether hormonal therapy should be given at the same time.

Side effects of radiation therapy might occur after a few weeks into treatment. Both types of radiation therapy may cause diarrhea and rectal bleeding due to radiation proctitis, as well as urinary incontinence and impotence. Symptoms tend to improve over time. Men who have undergone external beam radiation therapy will have a higher risk of later developing colon cancer and bladder cancer.

Cryosurgery is another method of treating prostate cancer. It is less invasive than radical prostatectomy, and general anesthesia is less commonly used. Under ultrasound guidance, metal rods are inserted through the skin of the perineum into the prostate. Highly purified Argon gas is used to cool the rods, freezing the surrounding tissue at −196° C. (−320° F.). As the water within the prostate cells freeze, the cells die. The urethra is protected from freezing by a catheter filled with warm liquid. Cryosurgery generally causes fewer problems with urinary control than other treatments, but impotence occurs up to ninety percent of the time. When used as the initial treatment for prostate cancer and in the hands of an experienced cryosurgeon, cryosurgery has a 10 year biochemical disease free rate superior to all other treatments including radical prostatectomy and any form of radiation Cryosurgery has also been demonstrated to be superior to radical prostatectomy for recurrent cancer following radiation therapy.

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It may also be given to certain men undergoing radiation therapy or surgery to help prevent return of their cancer.

Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

There are several forms of hormonal therapy. Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Antiandrogens are medications such as flutamide, bicalutamide, nilutamide, and cyproterone acetate which directly block the actions of testosterone and DHT within prostate cancer cells.

Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using antiandrogens.

GnRH action can be interrupted in one of two ways. GnRH antagonists suppress the production of LH directly, while GnRH agonists suppress LH through the process of down-regulation after an initial stimulation effect. Abarelix is an example of a GnRH antagonist, while the GnRH agonists include leuprolide, goserelin, triptorelin, and buserelin. Initially, GnRH agonists increase the production of LH. However, because the constant supply of the medication does not match the body's natural production rhythm, production of both LH and GnRH decreases after a few weeks.

As of 2006 the most successful hormonal treatments are orchiectomy and GnRH agonists. Despite their higher cost, GnRH agonists are often chosen over orchiectomy for cosmetic and emotional reasons. Eventually, total androgen blockade may prove to be better than orchiectomy or GnRH agonists used alone.

Each treatment has disadvantages which limit its use in certain circumstances. Although orchiectomy is a low-risk surgery, the psychological impact of removing the testicles can be significant. The loss of testosterone also causes hot flashes, weight gain, loss of libido, enlargement of the breasts (gynecomastia), impotence and osteoporosis. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer.

Bone pain due to metastatic disease is treated with opioid pain relievers such as morphine and oxycodone. External beam radiation therapy directed at bone metastases may provide pain relief. Injections of certain radioisotopes, such as strontium$^{89}$, phosphorus$^{32}$, or samarium$^{153}$, also target bone metastases and may help relieve pain.

High Intensity Focused Ultrasound (HIFU) for prostate cancer utilizes ultrasonic waves to ablate/destroy the tissue of the prostate. During the HIFU procedure, sound waves are used to heat the prostate tissue thus destroying the cancerous cells. Essentially, ultrasonic waves are precisely focused on specific areas of the prostate to eliminate the prostate cancer with minimal risks of effecting other tissue or organs. Temperatures at the focal point of the sound waves can exceed 100° C. The ability to focus the ultrasonic waves leads to a relatively low occurrence of both incontinence and impotence. (0.6% and 0-20%, respectively). According to international studies, when compared to other procedures, HIFU has a high success rate with a reduced risk of side effects. Studies using the Sonablate 500 HIFU machine have shown that 94% of patients with a pretreatment PSA (Prostate Specific Antigen) of less than 10 g/ml were cancer-free after three years. However, many studies of HIFU were performed by manufacturers of HIFU devices, or members of manufacturers' advisory panels.

HIFU was first used in the 1940's and 1950's in efforts to destroy tumors in the central nervous system. Since then, HIFU has been shown to be effective at destroying malignant tissue in the brain, prostate, spleen, liver, kidney, breast, and bone. Today, the HIFU procedure for prostate cancer is performed using a transrectal probe. This procedure has been performed for over ten years and is currently approved for use in Japan, Europe, Canada, and parts of Central and South America.

Although not yet approved for use in the Unites States, many patients have received the HIFU procedure at facilities in Canada, and Central and South America. Currently, therapy is available using the Sonablate 500 or the Ablatherm. The Sonablate 500 is designed by Focus Surgery of Indianapolis, Ind. and is used in international HIFU centers around the world.

Several medications and vitamins may also help prevent prostate cancer. Two dietary supplements, vitamin E and selenium, may help prevent prostate cancer when taken daily. Estrogens from fermented soybeans and other plant sources (called phytoestrogens) may also help prevent prostate cancer. The selective estrogen receptor modulator drug toremifene has shown promise in early trials. Two medications which block the conversion of testosterone to dihydrotestosterone, finasteride and dutasteride, have also shown some promise. As of 2006 the use of these medications for primary prevention is still in the testing phase, and they are not widely used for this purpose. The problem with these medications is that they may preferentially block the development of lower-grade prostate tumors, leading to a relatively greater chance of higher grade cancers, and negating any overall survival improvement. Green tea may be protective (due to its polyphenol content), though the data is mixed. A 2006 study of green tea derivatives demonstrated promising prostate cancer prevention in patients at high risk for the disease. In 2003, an Australian research team led by Graham Giles of The Cancer Council Australia concluded that frequent masturbation by males appears to help prevent the development of prostate cancer. Recent research published in the Journal of the National Cancer Institute suggests that taking multivitamins more than seven times a week can increase the risks of contracting the disease. This research was unable to highlight the exact vitamins responsible for this increase (almost double), although they suggest that vitamin A, vitamin E and beta-carotene may lie at its heart. It is advised that those taking multivitamins never exceed the stated daily dose on the label. Scientists recommend a healthy, well balanced diet rich in fiber, and to reduce intake of meat. A 2007 study published in the Journal of the National Cancer Institute found that men eating cauliflower, broccoli, or one of the other cruciferous vegetables, more than once a week were 40% less likely to develop prostate cancer than men who rarely ate those vegetables. Scientists believe the reason for this phenomenon has to do with a phytochemical called Diindolylmethane in these vegetables that has antiandrogenic and immune modulating properties. This compound is currently under investigation by the National Cancer Institute as a natural therapeutic for prostate cancer.

D. Urethral Cancer

Different types of treatments are available for patients with urethral cancer. Surgery is the most common treatment for cancer of the urethra. One of the following types of surgery may be done:

Open excision: Removal of the cancer by surgery.

Electro-resection with fulguration: Surgery to remove the cancer by electric current. A lighted tool with a small wire loop on the end is used to remove the cancer or to burn the tumor away with high-energy electricity.

Laser surgery: A surgical procedure that uses a laser beam (a narrow beam of intense light) as a knife to make bloodless cuts in tissue or to remove or destroy tissue.

Lymph node dissection: Lymph nodes in the pelvis and groin may be removed.

Cystourethrectomy: Surgery to remove the bladder and the urethra.

Cystoprostatectomy: Surgery to remove the bladder and the prostate.

Anterior exenteration: Surgery to remove the urethra, the bladder, and the vagina.

Plastic surgery may be done to rebuild the vagina.

Partial penectomy: Surgery to remove the part of the penis surrounding the urethra where cancer has spread. Plastic surgery may be done to rebuild the penis.

Radical penectomy: Surgery to remove the entire penis. Plastic surgery may be done to rebuild the penis.

If the urethra is removed, the surgeon will make a new way for the urine to pass from the body. This is called urinary diversion. If the bladder is removed, the surgeon will make a new way for urine to be stored and passed from the body. The surgeon may use part of the small intestine to make a tube that passes urine through an opening (stoma). This is called an ostomy or urostomy. If a patient has an ostomy, a disposable bag to collect urine is worn under clothing. The surgeon may also use part of the small intestine to make a new storage pouch (continent reservoir) inside the body where the urine can collect. A tube (catheter) is then used to drain the urine through a stoma.

Even if the doctor removes all the cancer that can be seen at the time of the surgery, some patients may be given chemotherapy or radiation therapy after surgery to kill any cancer cells that are left. Treatment given after the surgery, to increase the chances of a cure, is called adjuvant therapy.

Two types of radiation therapy are used with urethral cancer. External radiation therapy uses a machine outside the body to send radiation toward the cancer. Internal radiation therapy uses a radioactive substance sealed in needles, seeds, wires, or catheters that are placed directly into or near the cancer. The way the radiation therapy is given depends on the type and stage of the cancer being treated.

Chemotherapy for urethral cancer involves systemic treatment (i.e., destroys cancer cells throughout the body) that is administered orally or intravenously. Medications are often used in combination to destroy urethral cancer that has metastasized. Commonly used drugs include cisplatin (Platinol®), vincristine (Oncovin®), and methotrexate (Trexall®).

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Tissue Samples. The tumor and adjacent non-tumor tissue used in this study were obtained from untreated patients who were in surgery for bladder cancer. All patients provided written consent before the procedure. Samples were collected at the Urology and Nephrology Center in Mansoura, Egypt between August 1998 and April 2000. The bladder cancer tissue bank used in this study was established in 1992 and contains clinical data on all patients presenting with bladder cancer.

When needed for experiments, RNA was extracted from tissue samples using the TRIzol reagent.

Urine Samples. Urine samples were collected from patients already diagnosed with bladder cancer, patients exhibiting other urogenital disorders, and healthy volunteers. After collection on ice, samples were centrifuged at 3,000 g at 4° C. Urine sediments were washed twice with ice-cold PBS, resuspended in 1 ml PBS and transferred to 1.5 ml microfuge tubes. Specimens were then centrifuged at 3,000 g at 4° C. Supernatants were aspirated and urine sediment was resuspended in 1 ml TRIzol reagent.

When needed for experiments extraction of RNA from urine was completed using TRIzol.

ELISA Assay for TPβ vs. TPα urine sample analysis. Ninety-six-well plates were set up with antibodies to measure fluorescence as follows: The wells were coated with anti-TPβ antibody followed by a wash after binding time to remove all proteins but target. The plate was then blocked by addition of PBS followed by a wash. A rabbit anti-human secondary antibody was added to the target followed by a second wash. A goat anti-rabbit antibody with Horseradish Peroxidase (HRP) associated with it was added followed by a wash. 3,3',5,5'-tetramethylbenzidine was added to cause fluorescence of the HRP.

Fluorescence levels of the samples were measured using a Labsystems Multiskan RC micro-plate reader. (Fisher Scientific) Real Time semi-quantitative PCR for mRNA TPβ vs. TPα analysis. mRNA levels of TPα, and TPβ were compared using semi-quantitative real time PCR with cDNA from tissue and urine samples obtained from patients and normal controls. cDNA was prepared using Invitrogen's Super Script III first strand synthesis System for RT-PCR as per manufacturer's protocol.

Reactions were run using cDNA in a Light Cycler Thermocycler (Roche) with the following reaction conditions: 50° C. for 10 minutes and then 95° C. for 2 minutes followed by 55 cycles of the following: 95° C. for 10 sec., 56° C. for 20 sec., and 72° C. for 45 sec. Product levels were measured from incorporation of fluorescent double stranded DNA binding dye SYBR Green (Invitrogen). HPRT levels in samples were also measured for using in normalization.

Three reactions were run for each sample changing only the primers each time. (All primers are given in the 5 prime to 3 prime order and based on the following GenBank sequence GI numbers: 42518081 for TPβ and 117414146 for TPα) Primers used were: 1070 forward (ACGGAGAAG-GAGCT-GCTCATCT (SEQ ID NO:5)), complement to NTs 1070-1091 on TPβ and NTs 1070-1091 on TPα) and 1356 Reverse (CACTGTCCATCCAGCA-CCC (SEQ ID NO:6)), complement to NTs 1356-1338 on TPα, no complement on TPβ) for TPαdetection, 1070 Forward and 1378 Reverse (CAAAAG-GAAGCAACT-GTACCCC (SEQ ID NO:7)), complement to NTs 1399-1378 on TPβ and NTs 2039-2060 on TPα) for TPβ detection, and HPRT forward (CTTGCTCGAGATGT (SEQ ID NO:8)) and HPRT Reverse (GTCTGCATTGT-TTTGC-CAGTG (SEQ ID NO:9)) for HPRT detection (to be used as a normalization control).

Statistical Analysis. Raw data from real time PCR analyzed using linear regression methods using the LinRegPCR computer program version 7.5. (Program available upon request to email: bioinfo@amc.uva.nl; subject: LinRegPCR). Graph-Pad Prism 4 software was used to perform a Mann Whitney t-test on the data to check for statistical significance.

Raw fluorescence data from ELISA was analyzed for statistical significance in the same way using GraphPad Prism 4 software.

Example 2

Results mRNA Levels of TPα and TPβ Are the Same In Tumor and Non-Tumor Tissue Samples. In order to compare the level of TP receptor mRNA semi-quantitative real time PCR was performed on cDNA made from bladder tumors and adjacent non-cancer tissue. Levels of TPα and TPβ were measured and normalized.

Expression of TPα when measured showed no significant difference between tumor and adjacent non-tumor tissue (FIG. 1A) (P=0.9) Likewise, expression of TPβ showed no difference in expression between the two tissue types (FIG. 1B) (P=0.3)

mRNA Levels of TPα and TPβ in Urine Samples Do Not Differ Between Normal and Cancer Patients. To see how the levels of mRNA of TPα and TPβ compared in patient urine samples semi-QPCR was done on c-DNA prepared from samples. Comparison was done between bladder cancer patients, healthy individuals, and others exhibiting other urogenital disorders. The levels of TPα and TPβ mRNAs were determined and normalized.

Figure 2:
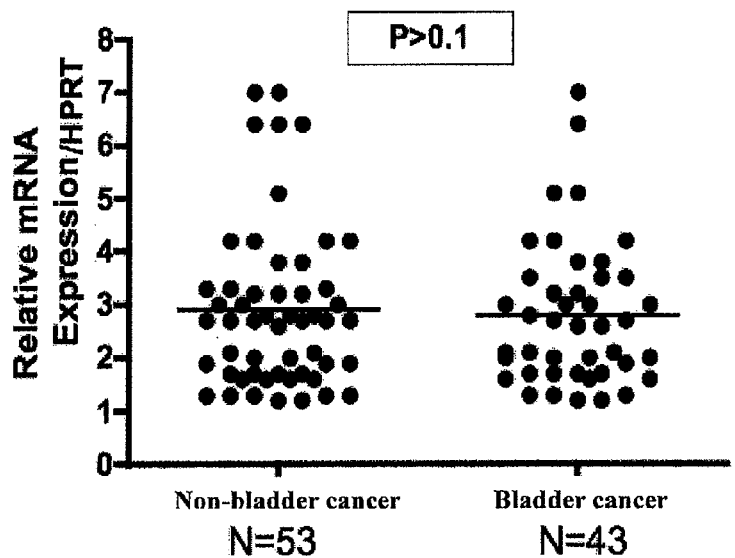
FIG. 2. TPβ mRNA Levels in Urine are Similar in Non-Bladder Cancer and Cancer Samples. mRNA was extracted from urine samples taken from healthy individuals and patients diagnosed with bladder cancer. cDNA was prepared and then run in real time PCR to measure levels of mRNA. The figure shows the expression level relative to HPRT amplified from the same sample. There is no statistically significant difference between the expression levels of the non-cancer group and the cancer group (P>0.1).

Levels of TPα and TPβ mRNAs showed no significant difference between urine taken from healthy individuals or those diagnosed with bladder cancer (FIG. 2). There was also no difference seen in TPα and TPβ mRNA levels compared to individuals exhibiting other urogenital disorders (P>0.1)

TPβ is Over-Expressed on the Protein Level in Cancer Patient Urine Samples. In order to determine the amount of TP receptor protein present in urine samples, TPα and TPβ protein levels were compared in urine samples from the aforementioned group using the ELISA assay.

Figure 3:
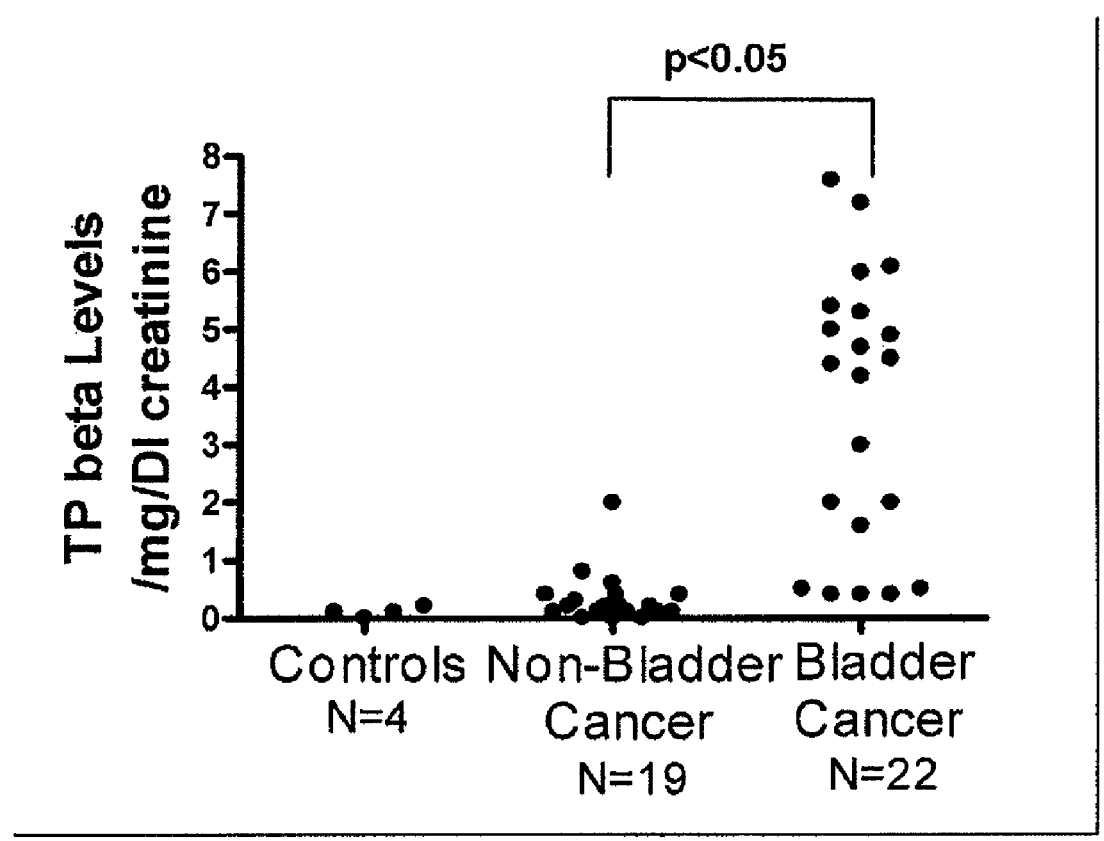
FIG. 3. TPβ Protein Levels are Higher in Urine Samples from Cancer Patients. Urine samples of a control group, non-bladder cancer patients, and patients diagnosed with bladder cancer were used as samples. TPβ protein levels were then detected by ELISA assay. The majority of bladder cancer samples showed much higher levels of TPβ than the non-cancer samples (P<0.05).

All but a small amount of the urine samples from bladder cancer patients exhibited significantly elevated levels of TPβ protein as compared to TPαlevels (FIG. 3) (P<0.05).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

U.S. Pat. No. 4,196,265
U.S. Pat. No. 4,313,734
U.S. Pat. No. 4,366,241
U.S. Pat. No. 4,632,901
U.S. Pat. No. 4,770,853
U.S. Pat. No. 4,786,589
U.S. Pat. No. 4,816,567
U.S. Pat. No. 4,867,973
U.S. Pat. No. 5,565,332
U.S. Pat. No. 5,656,448
Campbell, In: *Monoclonal Antibody Technology, Laboratory Techniques in Biochemistry and Molecular Biology*, Burden and Von Knippenberg (Eds.), Elseview, Amsterdam, 13:71-74/75-83, 1984.
Clark, *Curr. Opin. Urol.*, 19:241-247, 2007.
Coyle and Kinsella, *FEBS J.*, 272:1036-1053, 2005.
European Appln. EP-A 0 125 118
European Appln. EP-A 0 143 574
European Appln. EP-A 0 282 192
European Appln. EP-A 0 299 428
Gefter et al., *Somatic Cell Genet.*, 3:231-236, 1977.
Goding, In: *Monoclonal Antibodies: Principles and Practice*, 2d ed., Academic Press, Orlando, Fla., pp 60-61, 71-74, 1986.
Harlow and Lane, In: *Antibodies. A Laboratory Manual*, Cold Spring Harbor Laboratory, 1988.
Huang et al., *Cell. Signal.*, 16:521-533, 2004.
Jabbour et al., *Molec. Cell. Endocrin.*, 252:191-200, 2006.
Jemal et al., *CA Cancer J. Clin.*, 57:43-66, 2007.
Kohler and Milstein, *Eur. J. Immunol.*, 6:511-519, 1976.
Kohler and Milstein, *Nature*, 256:495-497, 1975.
Moussa et al., *Cancer Res.*, 65:11581-11587, 2005.
PCT Appln. WO 88/08534
Sengupta and Blute, *J. Urol.*, 67(Suppl 3A):48-55, 2006.
Takekoshi et al., *J. Biochem.*, 130, pp. 299-303, 2001.
Valentin et al., *Biochem. Biophys. Res. Comm.*, 329:898-904, 2005.
Wardemann et al. *Science*, 301(5638):1374-1377, 2003.

What is claimed:

1. A method of detecting bladder cancer in a subject comprising detecting elevated thromboxane receptor β protein expression, as compared to normal controls, in the urine of said subject.

2. The method of claim 1, wherein detecting comprises immunologic detection.

3. The method of claim 2, wherein immunologic detection comprises a lateral flow assay or an ELISA.

4. The method of claim 2, wherein immunologic detection comprises application of urine to a support comprising a first anti-thromboxane receptor antibody.

5. The method of claim 4, wherein immunologic detection further comprises exposing thromboxane receptor β bound to said first antibody to a second anti-thromboxane receptor antibody, said first and second anti anti-thromboxane antibodies binding to different epitopes.

6. The method of claim 5, wherein said second anti-thromboxane receptor antibody comprises a detectable label.

7. The method of claim 5, wherein said second anti-thromboxane receptor β antibody is detected using an anti-Fc antibody that is labeled with a detectable marker.

8. The method of claim 4, wherein said support is a membrane, a dipstick, a multi-well dish, a filter, a bead, or a biochip.

9. The method of claim 1, wherein the bladder cancer is invasive bladder cancer, superficial bladder cancer or metastatic bladder cancer.

10. The method of claim 1, wherein said subject previously has been diagnosed with bladder cancer and was successfully treated for said bladder cancer.

* * * * *

UNITED STATES PATENT AND TRADEMARK OFFICE
CERTIFICATE OF CORRECTION

PATENT NO. : 8,101,371 B2  
APPLICATION NO. : 12/253592  
DATED : January 24, 2012  
INVENTOR(S) : Omar Moussa et al.

It is certified that error appears in the above-identified patent and that said Letters Patent is hereby corrected as shown below:

In claim 5, column 41, line 24, delete "anti anti-thromboxane" and insert --anti-thromboxane-- therefor.

Signed and Sealed this  
Twenty-seventh Day of March, 2012

David J. Kappos  
*Director of the United States Patent and Trademark Office*